US012715882B2

(12) United States Patent
Galimberti et al.

(10) Patent No.: US 12,715,882 B2
(45) Date of Patent: Aug. 25, 2026

(54) ADDUCT COMPRISING AT LEAST A METAL SELECTED FROM GOLD, SILVER AND COPPER AND AN ADDUCT OF A CARBON ALLOTROP AND A PYRROLIC COMPOUND

(71) Applicant: POLITECNICO DI MILANO, Milan (IT)

(72) Inventors: Maurizio Stefano Galimberti, Milan (IT); Vincenzina Barbera, Biancavilla (IT); Gabriele Candiani, Milan (IT)

( * ) Notice: Subject to any disclaimer, the term of this patent is extended or adjusted under 35 U.S.C. 154(b) by 572 days.

(21) Appl. No.: 18/020,956

(22) PCT Filed: Aug. 11, 2021

(86) PCT No.: PCT/EP2021/072421

§ 371 (c)(1),
(2) Date: Feb. 13, 2023

(87) PCT Pub. No.: WO2022/034153

PCT Pub. Date: Feb. 17, 2022

(65) Prior Publication Data

US 2023/0295188 A1 Sep. 21, 2023

(30) Foreign Application Priority Data

Aug. 13, 2020 (IT) ........................ 102020000020113

(51) Int. Cl.

| | |
|---|---|
| ***C07F 1/00*** | (2006.01) |
| ***C01B 32/174*** | (2017.01) |
| ***C01B 32/194*** | (2017.01) |
| ***C01B 32/21*** | (2017.01) |
| ***C07D 207/325*** | (2006.01) |
| ***C09C 1/56*** | (2006.01) |

(52) U.S. Cl.

CPC ............ *C07F 1/005* (2013.01); *C01B 32/174* (2017.08); *C01B 32/194* (2017.08); *C01B 32/21* (2017.08); *C07D 207/325* (2013.01); *C09C 1/56* (2013.01); *C01B 2202/06* (2013.01)

(58) Field of Classification Search

CPC .......... C07F 1/005; C07F 1/10; C01B 32/174; C01B 32/194; C01B 32/21; C01B 2202/06; C07D 207/325; C09C 1/56

See application file for complete search history.

(56) References Cited

U.S. PATENT DOCUMENTS

| | | | | |
|---|---|---|---|---|
| 10,160,652 | B2 * | 12/2018 | Galimberti | C01B 32/194 |
| 10,231,458 | B1 | 3/2019 | Salam et al. | |

FOREIGN PATENT DOCUMENTS

| | | | | |
|---|---|---|---|---|
| WO | WO-2018087685 A1 * | 5/2018 | | C07F 7/1804 |
| WO | WO-2019162873 A1 * | 8/2019 | | C07D 207/323 |

OTHER PUBLICATIONS

International Search Report and Written Opinion of corresponding patent application No. PCT/EP2021/072421, dated Sep. 23, 2021, 9 pages.

* cited by examiner

*Primary Examiner* — Medhanit W Bahta
(74) *Attorney, Agent, or Firm* — Patterson Intellectual Property Law, PC

(57) ABSTRACT

The present invention relates to an adduct comprising metal particles and an adduct between an sp2 carbon allotrope and a pyrrole compound. In particular, the invention relates to an adduct comprising metal nanoparticles (NPs) and hydrophylic adducts between a sp2 carbon allotrope and a pyrrole compound. The metal preferentially copper, silver or gold. Such adduct is preferentially used for anti-bacterial activity.

18 Claims, 18 Drawing Sheets

ADDUCT COMPRISING AT LEAST A METAL SELECTED FROM GOLD, SILVER AND COPPER AND AN ADDUCT OF A CARBON ALLOTROP AND A PYRROLIC COMPOUND

The present invention relates to an adduct comprising metal particles and an adduct between an $sp^2$ carbon allotrope and a pyrrole compound.

In particular, the invention relates to an adduct comprising metal nanoparticles (NPs) and hydrophylic adducts between a $sp^2$ carbon allotrope and a pyrrole compound.

The metal preferentially belongs to the class of heavy transition metals such as copper, silver or gold.

Such adduct is preferentially used for anti-bacterial activity.

The bacterial resistance is an emergency of increasing importance. Already in 2003 it was written, in (Silvermore, 2003) "Most bacteria have multiple routes to resistance to any drug and, once resistant, can rapidly give rise to vast numbers of resistant progeny. Natural selection favors mechanisms that confer resistance with the least fitness cost and those strains that are least burdened by their resistance. Selection may also favor determinants that prevent their own counterselection and resistant strains with enhanced survival ability or virulence. To this genetic and biochemical potential must be added the wide variety of bacteria that cause opportunistic infections in vulnerable human patients and the fact that the numbers of vulnerable patients grow steadily with advances in other fields of medicine." Some years later it was written in (Fair 2014): "Bacterial resistance to antibiotics has been a recognized reality almost since the dawn of the antibiotic era, but only within the past twenty years has the emergence of dangerous, resistant strains occurred with a disturbing regularity." Hence, it is not surprising what written in (Slavin, 2017): "The continuous emergence of bacterial resistance has challenged the research community to develop novel antibiotic agents." Nowadays, the bacterial resistance is a full-blown phenomenon, as reported in (McEven, 2017): "Antimicrobial resistance is a global public health crisis that threatens our ability to successfully treat bacterial infections".

As it was written in (Gao, 2008) "the successful and explosive development of nanomaterials inevitably leads to their intersections with biology and medicine". In ISO/TS 80004, a nanomaterial is defined as the "material with any external dimension in the nanoscale or having internal structure or surface structure in the nanoscale", with nanoscale defined as the "length range approximately from 1 nm to 100 nm". Nano-objects, discrete pieces of material, such as NPs and among them metal NPs, are thus included in this definition. A nanomaterial, with respect to macroscopic structures, has a larger surface/volume ratio and can thus give rise to a larger interfacial area. Hence, the interfacial area between the surface of nanomaterials and microorganisms exponentially increases, decreasing the particle size.

As written in (Wang, 2017) "NPs are a viable alternative to antibiotics and appear to have high potential to solve the problem of the emergence of bacterial multidrug resistance."

Metal NPs are among the most promising novel antibiotic agents. As written in (Slavin 2017) metal NPs "have shown strong antibacterial activity in an overwhelming number of studies. It is hypothesized that NPs with antibacterial activities have the potential to reduce or eliminate the evolution of more resistant bacteria because NPs target multiple biomolecules at once, avoiding the development of resistant strains." They can find application in the industry of medical devices, wastewater treatment, food packaging, synthetic textiles and dentistry. In (Slavin 2017) it is also written: "Typically, smaller NPs have higher antibacterial activity". The larger surface area plays a key role in that (Karakoti, 2006). However, in (Slavin 2017) it is also written "However, some studies have shown that larger NPs are more effective, indicating that size alone is not the most important factor of their toxicity." Indeed, the type of metal has a dramatic influence. Always in (Slavin 2017) it is written: "The metals used for antimicrobial NP fabrication are almost exclusively heavy metals, which are classified as metals with a density>5 g/cm$^3$".

In particular, metals used for preparing metal NPs for antibacterial activity belong to the class of transition metals. The IUPAC definition (IUPAC, Compendium of Chemical Terminology, 2nd ed. (the "Gold Book") (1997). Online corrected version: (2006-) "transition element". doi: 10.1351/goldbook.T06456) states that a transition metal is "an element whose atom has a partially filled d sub-shell, or which can give rise to cations with an incomplete d sub-shell". In (Slavin 2017) it is written "This is important because a partially filled d orbital means that these metals are generally more redox active, facilitating the NP formation." Indeed, NPs are formed through the reduction of a salt of the transition metal, with a selected reducing agent". Moreover, in (Karakoti, 2006) it is written "Materials surface chemistry is vital in biological interaction."

The antimicrobial activity of nanomaterials could be exerted by the release of ions, molecules or atoms from nanomaterial surfaces. This is a contact-independent antimicrobial mechanism. In this case, metal NPs are used as the nanomaterials. With the term metal NPs one refers to metal in the elemental state and also to metal compounds, such as oxides. In (Slavin 2017), types of metal NPs used for their antibacterial activity are summarized. They were Ag, $Ag/CeO_2$, $CeO_2$, Au, $Al_2O_3$, $Cu_2O$, CuO, MgO, $Mg(OH)_2$—$MgCl_2$ $Mg(OH)_2$—$MgSO_4$, $Mg(OH)_2$—MgO, $TiO_2$, ZnO. Many of the cited works were based on Ag particles.

The antimicrobial activity of nanomaterials could be exerted by the bulk structure of the nanomaterial itself: contact-dependent antimicrobial mechanism. The inherent antibacterial features of these materials directly rely on the specific architecture of their surfaces. In particular, carbon nanomaterials were investigated. In the review (Maleki Dizaj 2015) it was reported that "carbon-based nanomaterials such as fullerenes, carbon nanotubes (CNTs) (especially single-walled carbon nanotubes (SWCNTs)) and graphene oxide (GO) nanoparticles" have strong antimicrobial properties. In the review (Al-Jumaili, 2017) it is written that "Carbon nanostructures (CNSs) such as fullerene, carbon nanotubes (CNTs), graphene and diamond-like carbon (DLC) have been demonstrated to have potent broad-spectrum antibacterial activities toward pathogens".

The antibacterial mechanism of NPs was deeply investigated, though not completely understood In the review (Wang, 2017) it is written: "the currently accepted mechanisms include oxidative stress induction, metal ion release, and non-oxidative mechanisms." More in detail, it is written: "metal NPs can change the metabolic activity of bacteria", "The ability of NPs to enter biofilms also provides a practical method to inhibit biofilm formation", "ROS-induced oxidative stress is an important antibacterial mechanism of NPs", where ROS means reactive oxygen species, "metal ions are slowly released from metal oxide and are absorbed through the cell membrane, followed by direct interaction with the functional groups of proteins and nucleic acids" "heavy metal ions can indirectly act as carriers of antimicrobial substances" NPs can "damage the cell membrane" "many critical cellular metabolic processes related to proteins are significantly reduced". Moreover it is written "The multiple simultaneous mechanisms of action against microbes would require multiple simultaneous gene mutations in the same bacterial cell for antibacterial resistance to develop; therefore, it is difficult for bacterial cells to become resistant to NPs." In particular, concerning the antibacterial activity of Ag, the scientific literature has not yet clearly established if the bactericidal effect could be elicited by $Ag^+$ cations or Ag metallic NPs deposited on a substrate, for example a carbon material. $Ag^+$ ions have the ability to bind prokaryotes protein thiol groups and cause their denaturation, bringing about dysfunctionalities in different metabolic processes (e.g. transmembrane active transport and antioxidant reactions), as discussed in (Davies, 1997), (de Moraes, 2015), (Li, 2010). Moreover, they have the ability to form complexes between $Ag^+$ ions and nucleic acids, transmembrane carriers and/or cellular wall, as reported in (Li, 2010). [58], [91]. Metallic Ag NPs catalyze the oxidative degradation of membranes and of the cytosolic content, leading to the bacterial cell death. As reported in (Davies, 1997), the metallic Ag in aqueous medium could act as an "oxygen reservoir", collecting oxygen atoms in its bulk, thanks to its electronic properties and lattice dimensions, leading to the formation of ROS (e.g. hydroxyl (—OH), epoxide (—O—) and carboxyl (—COOH) free radicals), and then, when interfacing with organic content, causing the complete destructive degradation of microorganisms through the membrane lipid peroxidation mechanism, as described in (Hassan, 2012). It is believed that $Ag^+$ ions are released and diffuse at a certain distance over time and that the metallic Ag oxidizing capability is effective only on cells which are in direct contact with NPs and is practically instantaneous (Davies, 1997).

In particular, concerning the antibacterial mechanism of carbon nanomaterial, in the review (Maleki Dizaj 2015) it was written "Reviewed literature shows that the size of carbon nanoparticles plays an important role in the inactivation of the microorganisms. As major mechanism, direct contact of microorganisms with carbon nanostructures seriously affects their cellular membrane integrity, metabolic processes and morphology." And in the review (Al-Jumaili, 2017) it was written "In principle, the bactericidal action of CNSs typically involves a combination of physical and chemical mechanisms. Physically, CNSs may cause considerable structural damage to the cell wall and membrane of the microorganism." It is widely acknowledged that graphene and CNTs are the most investigated nanosized $sp^2$ carbon allotropes.

Concerning the antimicrobial activity of graphene, at least two mechanism of antibacterial action rely on the structure of graphene layers. They act as nanoknives: bacterial membranes are damaged by sharp edges, as reported in (Zhou 2016). Moreover, they are able to wrap/trap cells thanks to the is high flexibility. In (Al-Jumaili, 2017) it was written "Furthermore, carbon nanomaterials such as graphene sheets are capable to biologically isolate cells from their microenvironments, which may eventually lead to cell death." The third mechanism hypothesized for the antimicrobial activity of graphene involve oxidative stress due to the oxygenated groups of oxidated carbon allotropes. In (Al-Jumaili, 2017) it was written "Chemical interaction between CNSs and the microorganism surface may lead to generation of toxic substances, such as reactive oxygen species (ROS), placing the cell under oxidative stress. The interactions between CNSs and cells may cause an electron transfer phenomenon, where electrons are progressively drained from the microbial outer surface, which may cause ROS-independent oxidative stress, leading to the biological death".

Concerning MWCNTs, it was reported in (Maas, 2016) that they could act as nanodarts. A significantly higher bactericidal effect was reported (Kang, 2008) for SWCNTs with respect to MWCNTs and the different diameter (0.9 nm and 30 nm, respectively) was considered as the main factor. Higher expression of genes related to cell damage for SWCNTs was detected, suggesting a size-dependent bactericidal mechanism involving membrane disruption.

One of the problems in using metal NPs is the relatively poor dispersity and rapid leaching and their tendency to form aggregates. As reported in (Zhu, 2017), "to solve the above issues, an effective strategy is the attachment of the nanoparticles (Ag NPs in the case of this paper) to substrates, which can provide adequate active sites for the immobilization".

Hybrid systems based on metal NPs supported on carbon materials are available in the prior art. Ag NPs are the preferred ones, because of "their wide spectrum of antimicrobial properties, good stability, long-term antibacterial activity and low propensity to induce microbial resistance", as reported in (Zhu 2017). In (Han, 2019) it was written "Pristine and modified graphene are excellent carriers of Ag nanoparticles due to their large specific surface area and other properties. Graphene/Ag nanocomposite shows higher antibacterial performance than graphene and Ag". Such a good performance is justified on the basis of this mechanism "First, this nanocomposite can adhere and accumulate on the cell membranes by puncturing the membranes; second, Ag ions released from the nanocomposite undergo a reaction". It is acknowledged in the prior art that supportation of metal NPs should occur on carbon substrates containing oxygenated functional groups. In fact, solubility of the graphitic based hybrid should be obtained. In (Liu, 2011) it was reported the loss of bactericidal efficacy due to the lack of oxidized moieties. A correlation was suggested between the bactericidal efficacy and the size and dispersion state of materials. It would be thus desirable to use hybrid systems based on graphene layers and bactericidal NPs, with a mild oxidation of the layers. Indeed, a mild oxidation is desired to have at the same time dispersibility and a bulk graphitic structure not dramatically affected or, ideally, substantially unaltered.

In the case of graphene related materials, the prior art teaches the beneficial effects of using GO, that means graphene oxide, as the carbon nanomaterial. In (Szunerits, 2016) it is written "By growing Ag NPs on the surface of GO, several groups using different approaches have synthesized GO-Ag NP and rGO-Ag NP nanocomposites with significantly improved antibacterial activities when compared to GO and Ag NPs taken separately". The method reported in (Zhou, 2018) moves from Graphene Oxide. The GO powder was dispersed in deionized water to form the GO aqueous suspension after 30 min vigorous stirring and 1 h sonication. Then, silver nitrate aqueous was next mixed with GO aqueous suspension. After vigorous stirring, the Ag ions did adsorb onto the surface of GO sheets to form the $Ag^+$/GO mixture after 30 min sonication. Then, the $Ag^+$/GO powder was obtained by centrifugation, following the freeze-drying process. Finally, the Ag NPs/GE composited can be obtained by thermal annealing process in a tube furnace. In (Han, 2019) it is written: "GO/Ag composite materials can be produced by in situ reduction, immobilization, microwave assistant reduction, and plasma modification. In the reduction process, $Ag^+$ (usually $AgNO_3$)

initially combines with the functional groups of GO (negative charge) via electrostatic interactions." Then, the $Ag^+$ was in situ reduced to Ag NPs by means of various reducing agents, such as hydrazine, thiols and hydroquinone. Always in (Han, 2019) other methods are reported for supporting Ag NPs on graphene layers, "such as heating the mixture of raw material and a two phase process, synthesizing Ag NPs in organic solvent and then adding to a GO-containing water solution.

All the studies reported herein above are based on GO, which has to be prepared through the oxidation of a graphitic substrate, by applying an oxidation reaction characterized by harsh and dangerous reaction conditions (References).

In (Surudzic 2016) silver/poly(vinyl alcohol)/graphene nanocomposites were obtained by electrochemical method, with nominally graphene from the market. Graphene was added to dissolved PVA under vigorous stirring. After the solution was cooled to room temperature and sonicated, $KNO_3$ and AgNO3 were added to obtain a final given concentration. Electrochemical reduction of silver ions was performed galvanostatically. Hence, PVA was in the composite and a multistep procedure based on wet chemistry was used.

In (Yu, 2014), a sandwich-like antibacterial reagent (Ag/HNTs/rGO) was constructed through the direct growth of Ag NPs on the surface graphene-based HNTs nanosheets. Halloysite NTs (HNTs) were covered with a layer of self polymerized dopamine (DOPA) and Ag NPs adhered on the surface thanks to the adhesive properties of self polymerized DOPA.

In (Zhao, 2016) graphene-wrapped Ag nanowires were prepared by forming a graphene film through a large-area chemical vapor deposition (CVD).

The methods reported in the literature for forming the graphene/Ag NPs adducts involve many reaction steps, wet chemistry, are not highly efficient and are in most cases troublesome.

Hybrid systems with GO and transition metals other than silver have been as well reported in the prior art.

In (Moosavi 2015), iron oxide NPs were synthesized according to the co-precipitation method. $FeCl_3 6H2O$ and $FeCl_2 4H_2O$ (2.5 mg) were added to DI water and kept under mechanical agitation in $N_2$ atmosphere. Then, $NH_3$ was added dropwise and stirred for 4 h at 90° C. The resulting black precipitate was washed several times with DI water and kept for freeze-drying. For the synthesis of [GO+Iron Oxide (IO)] nanocomposite, GO was dispersed in DI water by ultra-sonication first. Then the salts, $FeCl_3$ and $FeCl_2 4H_2O$ were added to the GO dispersion in DI water, following the similar method described above for IO NPs. The final product was filtered, washed at least 3 times by DI water and the precipitate was freeze-dried.

Hybrid systems with silver particles with bactericidial activity were as well prepared with CNT as the carbon material.

In (Fan, 2019) Ag NPs were encapsulated in CNTs. CNTs were first treated with a mixture of acids with concentrated $H_2SO_4$ and $HNO_3$. After being washed with deionized water three times, a portion of carboxylated CNTs was adequately dispersed into deionized water in an ultrasonic bath for 1 h. Then, $AgNO_3$ solution was added into the CNTs suspension dropwise with constant stirring at 90° C. for 6 h. Following this, the samples were washed with absolute ethanol two times and added into an aqueous $NaBH_4$ solution. The final Ag-CNTs were obtained by drying at 40° C. overnight.

In (Xia, 2018), the original CNTs mixed with concentrated nitric acid heated at 100° C. for 5 h, while constantly stirring to prevent bruising. Then, functionalized CNTs are washed by deionized water and kept at 60° C. overnight. The functionalized CNTs were dehydrated at 120° C. in vacuum for 5 h. Then, silver nitrate ($AgNO_3$), concentrated aqueous ammonia ($NH_3*H_2O$) and glucose ($C_6H_{12}O_6$) were prepared to form 0.5 mL of a mixed solution, which was infiltrated into CNTs by wetness impregnation at room temperature. The impregnated sample ($CNTs/C_6H_{12}O_6/NH_3 \cdot H_2O/AgNO_3$/water) was immediately transferred into the oven at 60° C. for 1 h, after that the collected samples were washed using deionized water and dried overnight. Finally, the Ag-NPs encapsulated into CNTs with 4 wt % silver loading were obtained.

Hybrid systems with silver particles with bactericidial activity were as well prepared with fullerene as the carbon material, in the prior art.

In (Moor, 2016), C70 fullerene and Ag NPs were claimed to work in tandem to provide virucidal and bactericidal activities, respectively. Poly(styrene-block-poly4-vinylpyridine) was used as a template, allowing C70 integration into PS domains and in situ formation of Ag NPs in Poly (4VinilyPyridine) domains. Also in this case, it is clear the complexity of the multistep process.

Hybrid systems with silver particles with bactericidial activity were as well prepared with carbon black (CB) as the carbon material, in the prior art.

In (AG5 . . . ) Ag NPs were supported on chitosan (CS)-CB fibers. CB-CS nanocomposite was obtained by dissolving CS in acetic acid, adding water and then CB. Extrusion of the previous solution with concentrated $NH_3*H_2O$, evaporation of $NH_3*H_2O$ and drying at r.t. led to the fibers. $AgNO_3$ were dissolved in water and the dry fibers were added, then collected and dried. CB-CS fibers loaded with Ag were put in $NaBH_4$ solution and the metal ions were reduced to their clusters. The hybrid has bacericidial activity.

Hybrid systems with Au NPs on graphitic substrates containing heteroatoms such as graphitic carbon nitride were as well prepared.

In (Nguyen, 2019), graphitic carbon nitride was prepared via the thermal exfoliation of bulk graphitic carbon nitride. Bulk graphitic carbon nitride powder was first prepared using a modified thermal oxidation etching method by heating thiourea in a covered alumina crucible in a muffle furnace at 550° C. for 2 h at a rate of 15° C. $min^{-1}$. The yellow powder product was then well-milled in an agate mortar after cooling naturally to room temperature. The ground bulk graphitic carbon nitride was again heated at 550° C. for 2 h in air at a rate of 15° C. $min^{-1}$. Finally, a pale yellow powder consisting of graphitic carbon nitride nanosheets was obtained. 2.2. Au@(graphitic carbon nitride) was synthesized by the photodeposition method. Generally, graphitic carbon nitride nanosheets were dispersed in deionized water and ultrasonicated to obtain a homogeneous dispersion. $HAuCl_4$ aqueous solutions were then added into the above suspension dropwise under vigorous stirring for 30 min at room temperature. The Au NPs were deposited onto the graphitic carbon nitride by the photo-reduction of Au(III) under the irradiation of an UV lamp. Isopropanol was also added into the solution as hole scavenger. The resultant nanocomposite was separated by centrifugation and washed with deionized water several times. Finally, the Au@(graphitic carbon nitride) nanocatalyst was obtained by drying at 80° C. overnight in a vacuum oven and was used for the enhanced catalytic reduction of nitrophenols by sodium borohydride All the above reported pieces of prior art demonstrate that the antibacterial activity of mteal NPs based on heavy transition metals is well known and documented. Moreover it is documented the antibacterial activity of nanosized $sp^2$ carbon allotrope, though the interpretation can be controversial as reported in (Hegab, 2016) for graphene related materials. Moreover, it is documented the preparation of hybrid nanocomposites based on $sp^2$ carbon allotropes and heavy transition metals compounds and it is documented the antibacterial activity. The examples suggest the importance of anchoring the transition metal compound and indicate the oxidation of the carbon substrate as the preferred tool for promoting the anchoring. However, all the methods reported in the prior art for creating hybrid nanocomposites with a carbon substrate and metal NPs are based on wet chemistry, multistep procedures, in many cases complex and even troublesome, with even harsh and dangerous experimental conditions. The scalability of the reported methods to a larger scale appears to be problematic.

It would be highly desirable to prepare hybrid systems based on $sp^2$ carbon allotropes and heavy transition metals with antibacterial activity, named as the "adduct", by means of a simple and sustainable procedure, ideally in few steps, avoiding harsh reaction conditions and ideally, wet chemistry reactions based on organic solvents.

In particular, it would be desirable, for the preparation of the adduct, to avoid the use of toxic and hazardous solvents, such as for example halogenated and/or aromatic solvents.

It would be desirable that the solvent, whether needed, could be water.

It would be desirable, for the preparation of the adduct, to avoid high temperatures.

It would be indeed desirable that the $sp^2$ carbon allotrope could be selected among all the known $sp^2$ carbon allotropes, preferentially: furnace carbon black, carbon nanotubes, nanosized graphite, graphene and graphene related materials.

It would be desirable that the adduct could be easily isolated.

It would be desirable that the antibacterial activity could be expressed in mild conditions.

It would be indeed desirable that the adduct could be used for more cycles.

These and other objects of the present invention are achieved by means of an adduct according to claim 1.

In particular by means of an adduct of a metal selected from the group consisting of: copper, silver, gold, or mixture thereof; with an adduct of:

a $sp^2$ carbon allotrope and/or its derivative and compound of formula (I)

(I)

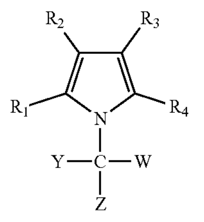

wherein $R_1$, $R_2$, $R_3$, $R_4$ are independently selected from the group consisting of: hydrogen, alkyl $C_1$-$C_3$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkynyl-aryl $C_2$-$C_6$ linear or branched, heteroaryl, and Y, Z e W are independently selected from the group consisting of hydrogen, alkyl $C_1$-$C_6$, alkenyl or alkynyl $C_2$-$C_6$ linear or branched, or selected from the from the group consisting of:

(A)

(B)

(C)

(D)

(E)

(F)

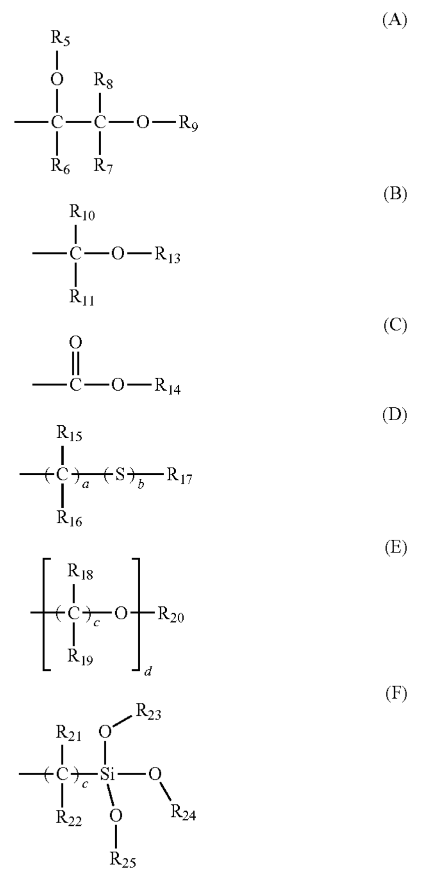

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, are independently selected from the group consisting of hydrogen, alkyl $C_1$-$C_6$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkenyl-aryl $C_2$-$C_6$ linear or branched, heteroaryl and carboxyl, and wherein b is an integer from 1 to 4 and a, c, d and e are, independently, integers from 1 to 12.

With the adduct according to the present invention a large selectivity in the H/D exchange reaction is obtained.

Preferably said metal is silver.

Preferably $R_1$, $R_2$, $R_3$, and $R_4$ are independently selected from the group consisting of: H, $CH_3$, $CH_2CH_3$, $CH_2CH_2CH_3$, phenyl.

Preferably said carbon allotrope or its derivative is selected from the group consisting of: carbon black, fullerene, Buchminstefullerenes, carbon nanohorns, carbon nanotubes, single-walled or multi-walled, carbon nanobuds, graphene, bilayer graphene, few-layer graphene, graphenylene, ciclocarbons, graphites with a number of stacked graphene layers from 2 to 10000.

Preferably said carbon allotrope derivative contains functional groups selected from the group consisting of:

functional groups containing oxygen, preferably hydroxyls, epoxies;

functional groups containing carbonyls, preferably aldehydes, ketones, carboxylic acids;

functional groups containing nitrogen atoms, preferably amines, amides, nitriles, diazonium salts, imines;

functional groups containing sulfur atoms, preferably sulfides, disulfides, sulfinates, sulfoxides, mercaptans, sulfones, sulfinic, sulfoxylic, and sulfonic groups.

In this way a vast range of carbon allotropes is available.

Preferably said derivative of said carbon allotrope is graphite oxide.

Preferably said derivative of said carbon allotrope is graphene oxide.

A further object of the present invention is to provide process for the preparation of an adduct according to to claim 1, comprising the steps of:

i. providing a solution and/or suspension of a compound of formula (I) in a protic or aprotic polar solvent;
ii. providing a mixture of the carbon allotrope in a protic or aprotic polar solvent used for the preparation of the solution and/or suspension referred to in step i.;
iii. mixing said solution and/or suspension (i) and said mixture (ii);
iv. stirring;
v. if necessary, removing said solvent from said mixture obtained in step iii
vi. providing energy;
vii. if necessary, dispersing the obtained mixture in the protic or aprotic polar solvent;
viii. adding a salt of the metal soluble in the selected protic or aprotic polar solvent;
ix. stirring;
x. if necessary, removing said solvent from the obtained mixture.

The process optionally comprising the additional steps of:

xi. if necessary, dispersing the mixture obtained after step vi in the protic or aprotic polar solvent;
xii. adding a reducing agent;
xiii. stirring;
xiv. removing said solvent from the obtained mixture.

Preferably said reducing agent is selected from the group consisting of: alcohols, aldehydes, carboxylic acids, Preferably said reducing agent is present in an equimolar amount respect to the transition metal salts.

Preferable reducing agents are selected from the group consisting of diols, triols and reducing sugars such as glucose, dextrose, fructose; hydrides such as $NaBH_4$, $LiAlH_4$; organic acids such as ascorbic acid, citric acid.

According to the present invention, the term reducing agent is referred to an agent that allows the complete transfer of one or more electrons to a molecular entity (also called 'electronation'), and, more generally, the reverse of the processes described under oxidation (2) and (3). (*PAC,* 1994, 66, 1077. (*Glossary of terms used in physical organic chemistry* (*IUPAC Recommendations* 1994)) on page 1160 [Terms] [Paper] Cite as: *IUPAC. Compendium of Chemical Terminology, 2nd ed*. (the "*Gold Book*"). Compiled by A. D. McNaught and A. Wilkinson. *Blackwell Scientific Publications*, Oxford (1997). Online version (2019-) created by S. J. Chalk. ISBN 0-9678550-9-8. https://doi.org/10.1351/goldbook.)

Oxidizing and reducing agents are key terms used in describing the reactants in redox reactions that transfer electrons between reactants to form products. This page discusses what defines an oxidizing or reducing agent, how to determine an oxidizing and reducing agent in a chemical reaction, and the importance of this concept in real world applications.

According to the present invention, an oxidizing agent, or oxidant, gains electrons and is reduced in a chemical reaction. Also known as the electron acceptor, the oxidizing agent is normally in one of its higher possible oxidation states because it will gain electrons and be reduced. Examples of oxidizing agents include halogens, potassium nitrate, and nitric acid.

According to the present invention, a reducing agent, or reductant, loses electrons and is oxidized in a chemical reaction. A reducing agent is typically in one of its lower possible oxidation states, and is known as the electron donor. A reducing agent is oxidized, because it loses electrons in the redox reaction. Examples of reducing agents include the earth metals, formic acid, and sulfite compounds."

The adduct according to the present invention will be better illustrated through the examples set down below, which illustrate the operating steps of the process for the preparation of this adduct.

Characteristics and advantages of the invention will be more apparent from the description of preferred embodiments, shown by way of non-limiting example in the accompanying drawings, wherein.

Figure 14:
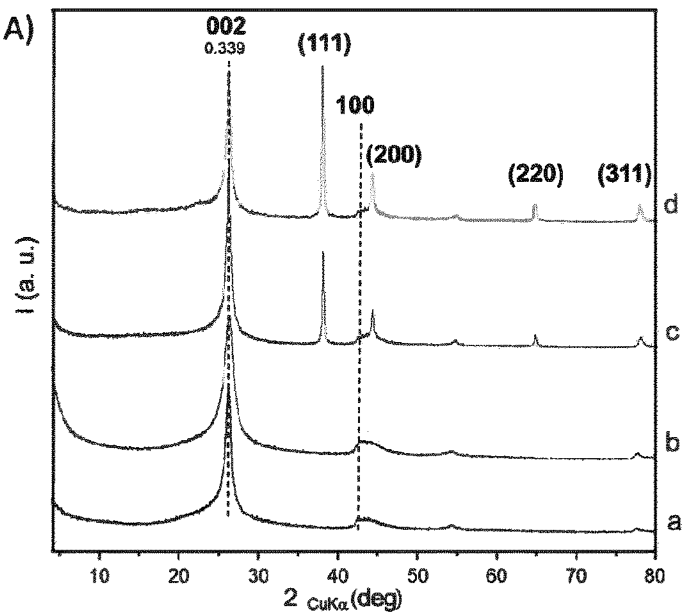
Figure 14:
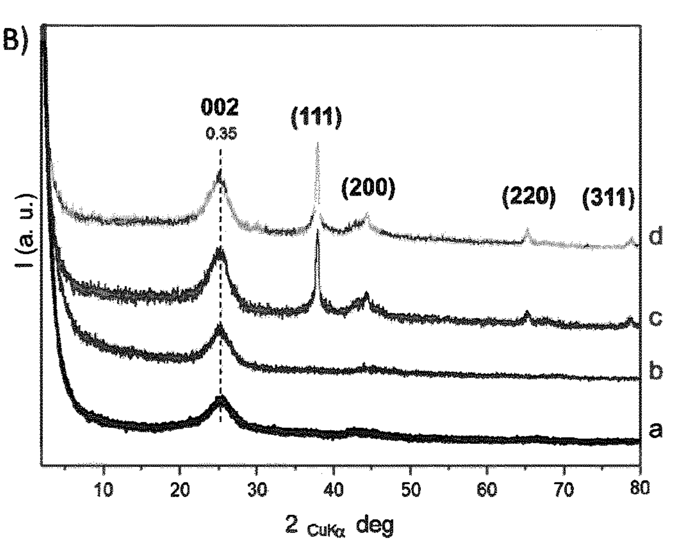
Figure 14:
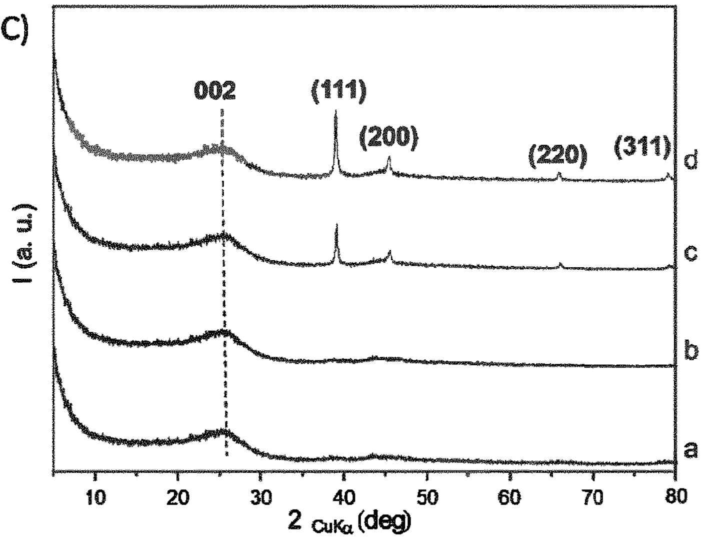
Figure 15:
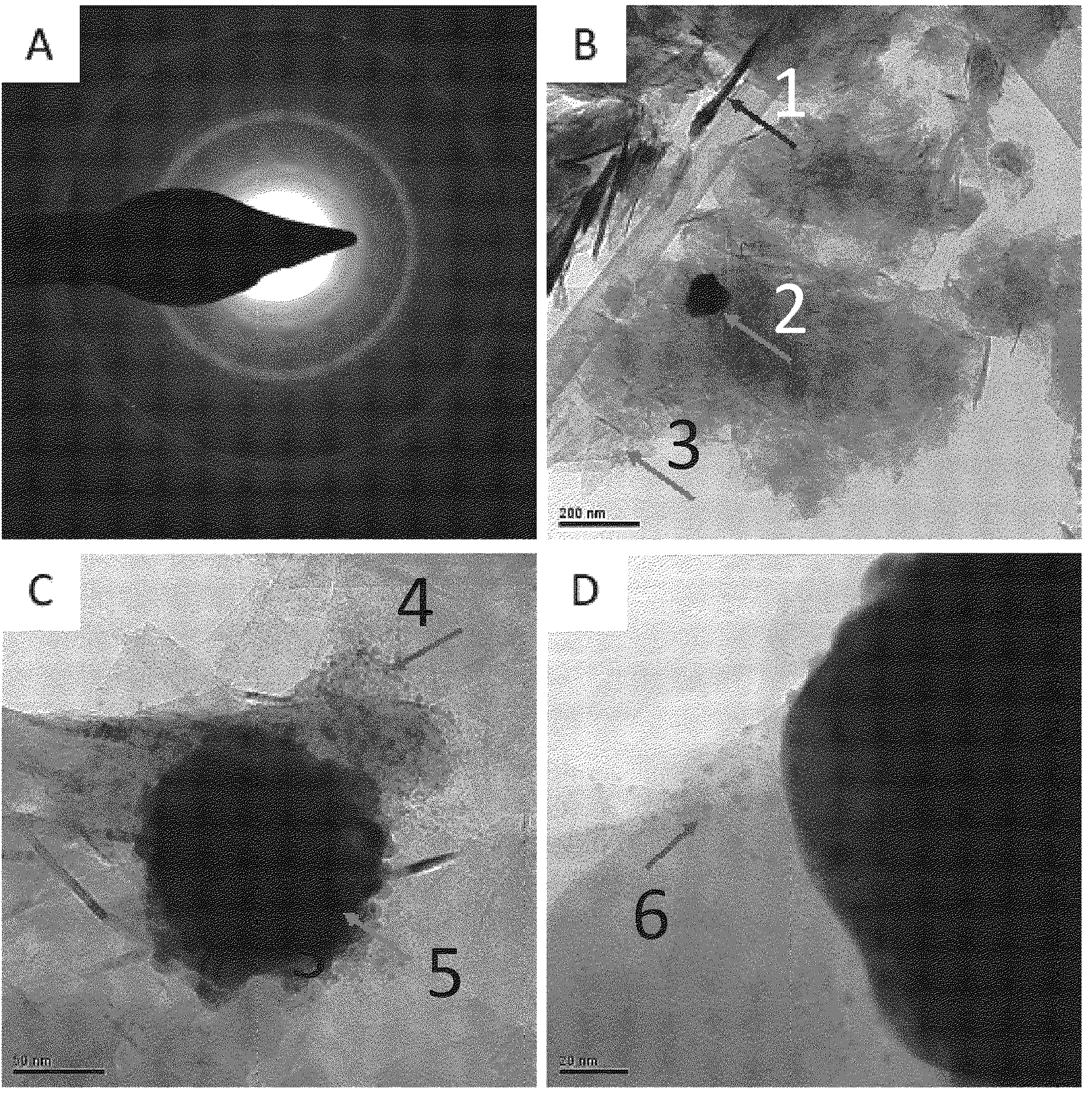
Figure 16:
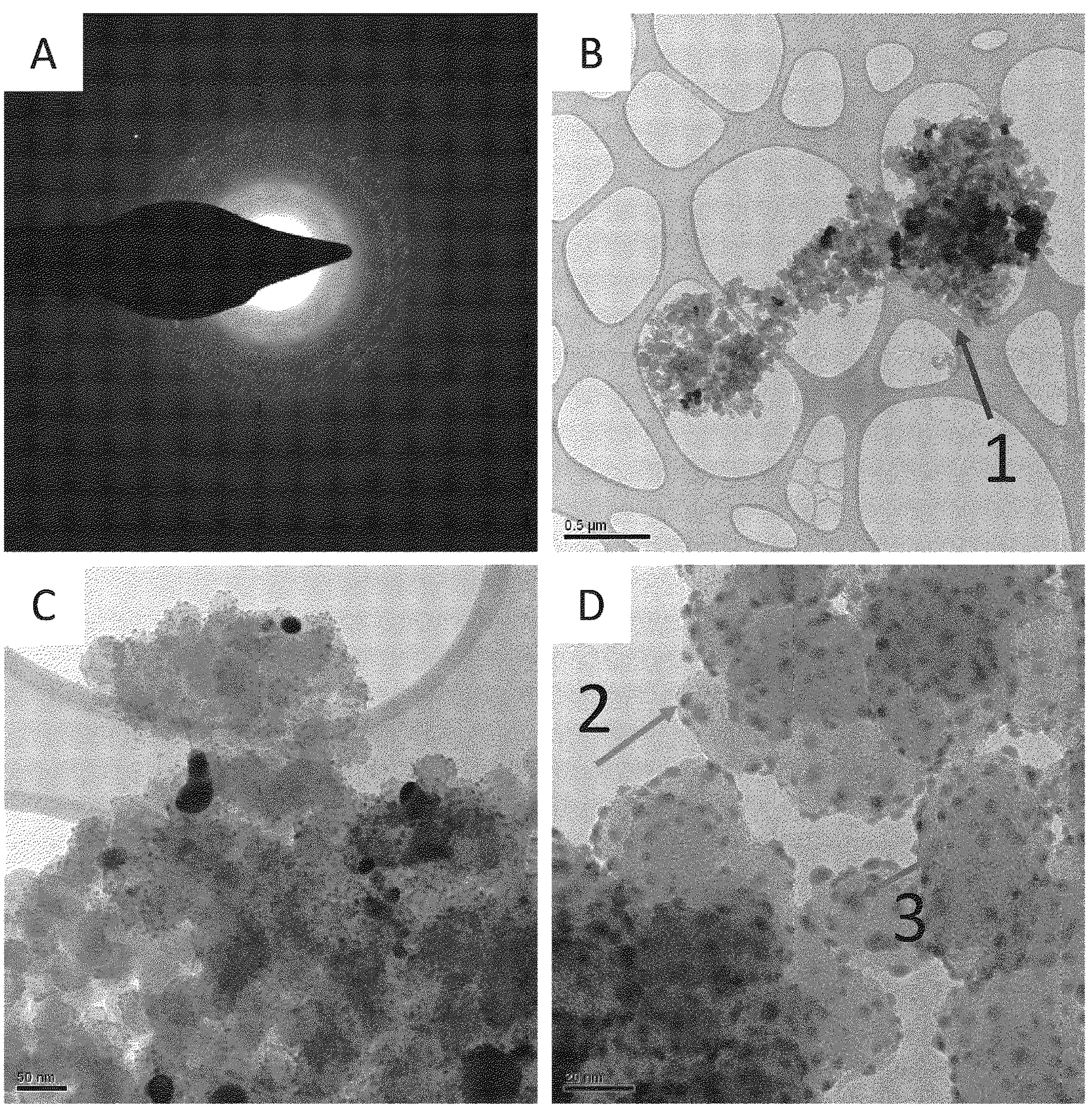
Figure 17:
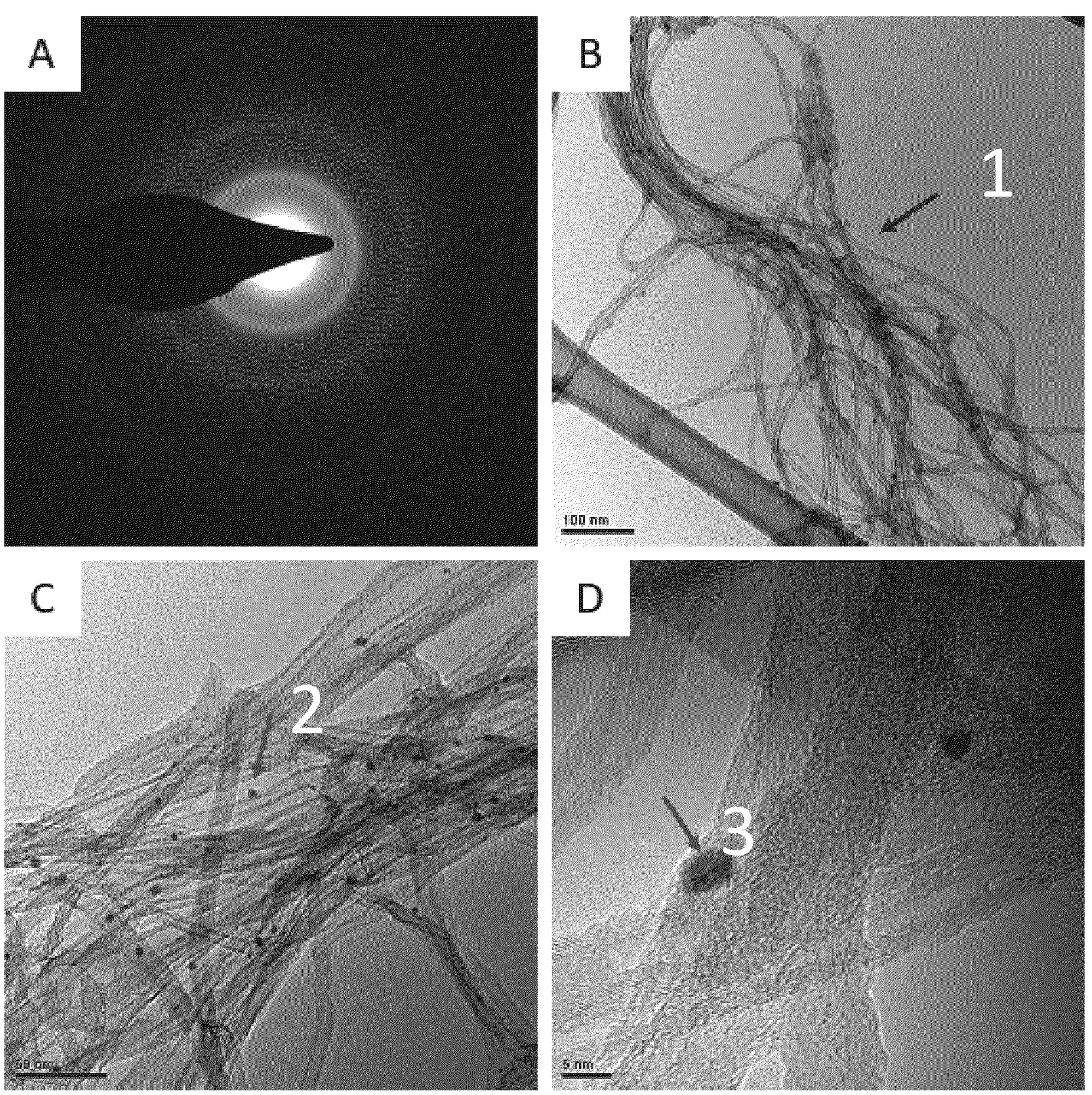

FIG. 14 A shows the XRD patterns of Graphite Nano 307 (HSAG) (a), HSAG-SP (b), HSAG-SP/Ag 350 (c) and HSAG-SP/Ag 650 (d);

FIG. 14 B shows the XRD patterns of MWCNT NC7000 (CNT) (a), CNT-SP (b), CNT-SP/Ag 350 (c) and CNT-SP/Ag 650 (d);

FIG. 14 C shows the XRD patterns of CB N326 (a), CBN326-SP (b), CBN326-SP/Ag 350 (c) and CBN326-SP/Ag 650 (d);

FIG. 15 shows the HRTEM micrographs for the sample HSAG-SP/Ag 650. Diffraction pattern § (A). Scalebar: 200 nm (B), 50 nm (C), 20 nm (D);

FIG. 16 shows the HRTEM micrographs for sample CBN326-SP/Ag 650. Diffraction pattern (A), Scalebar: 500 nm (B), Scalebar: 50 nm (C) and 20 nm (D);

FIG. 17 shows the HRTEM micrographs for sample CNT-SP/Ag 650. Diffraction pattern (A). Scalebar: 100 nm (B). Scalebar: 50 nm (C). Scalebar 5 nm (D).

Figure 18:
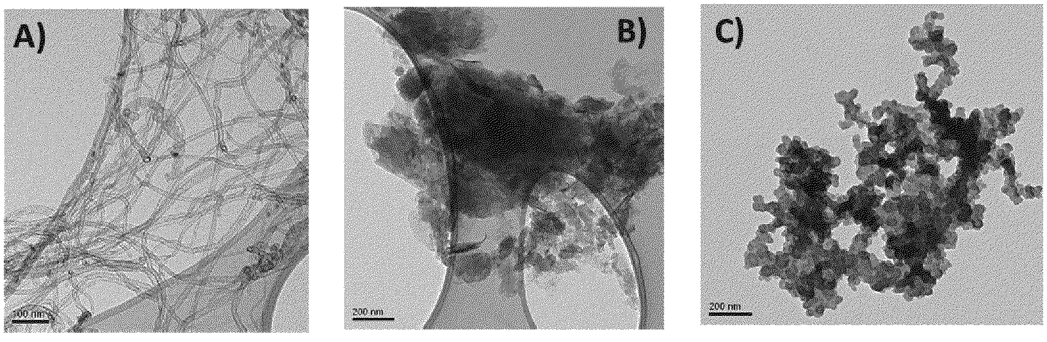

FIG. 18 shows the HRTEM micrographs for sample of example 22 (A), 24 (B) and 26 (C) (Comparison examples)

Figure 19:
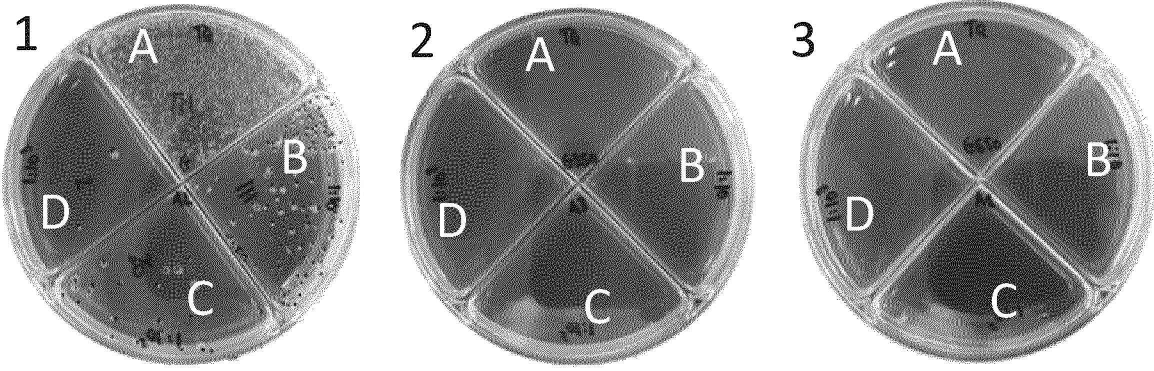
Figure 20:
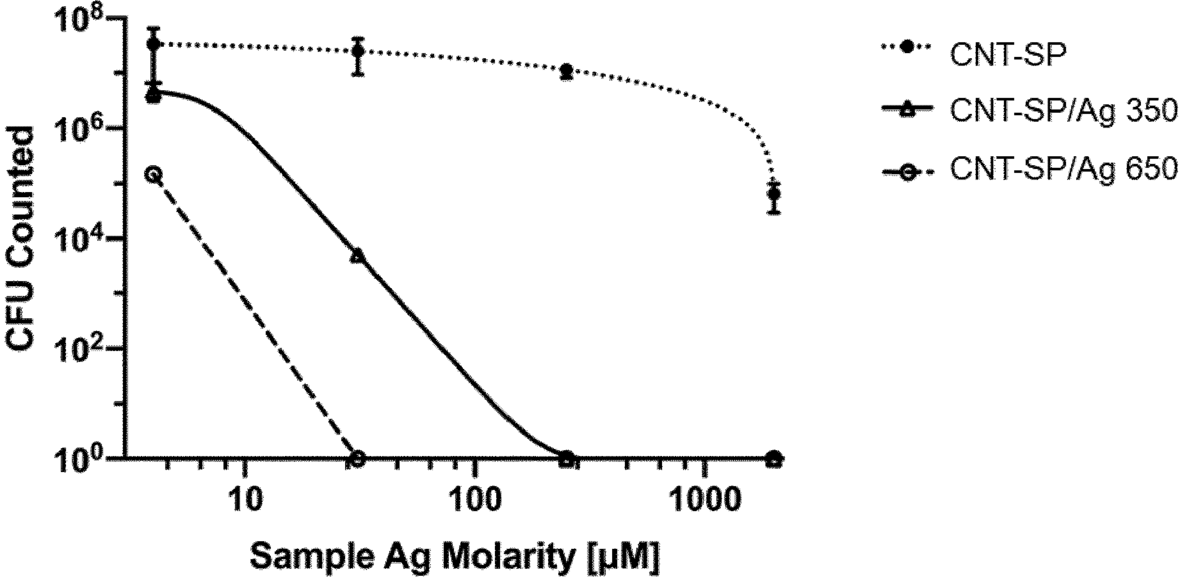
Figure 21:
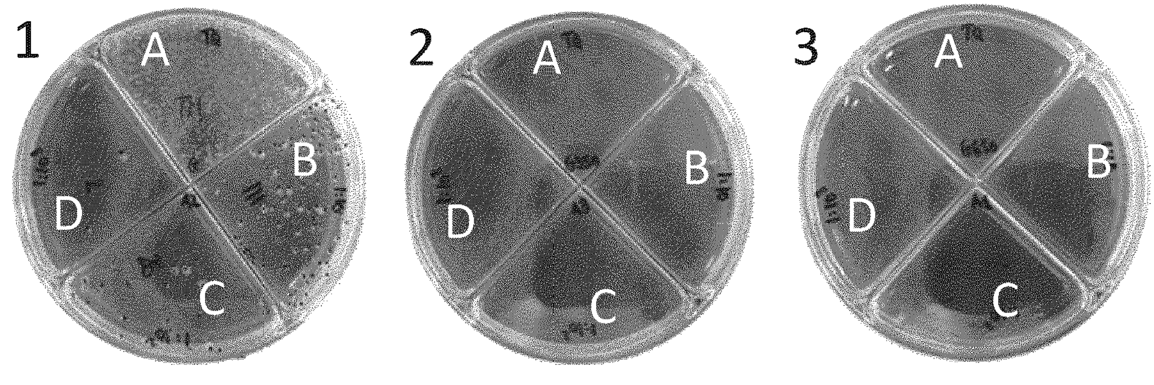
Figure 22:
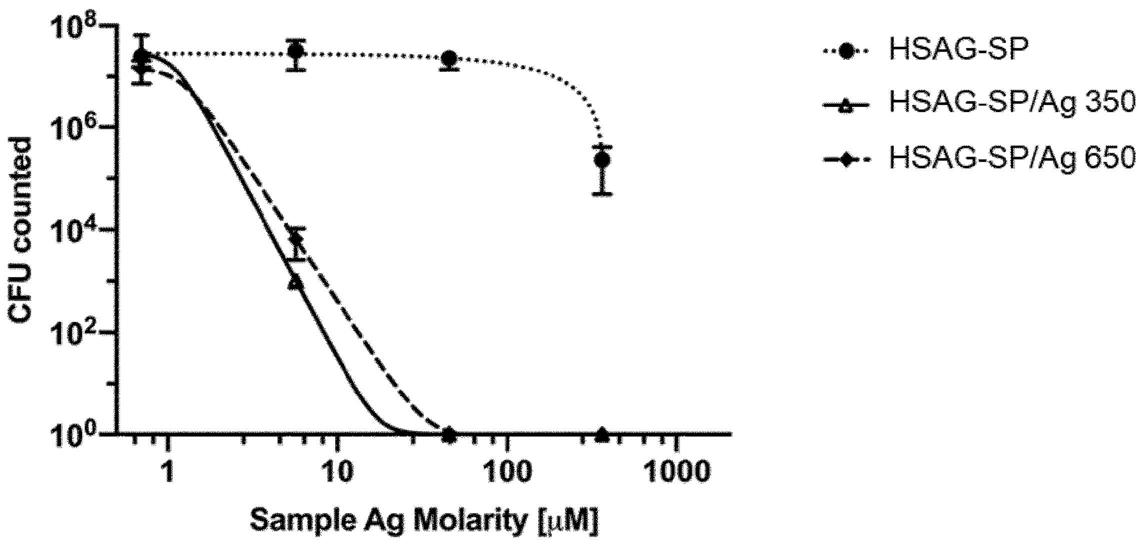
Figure 23:
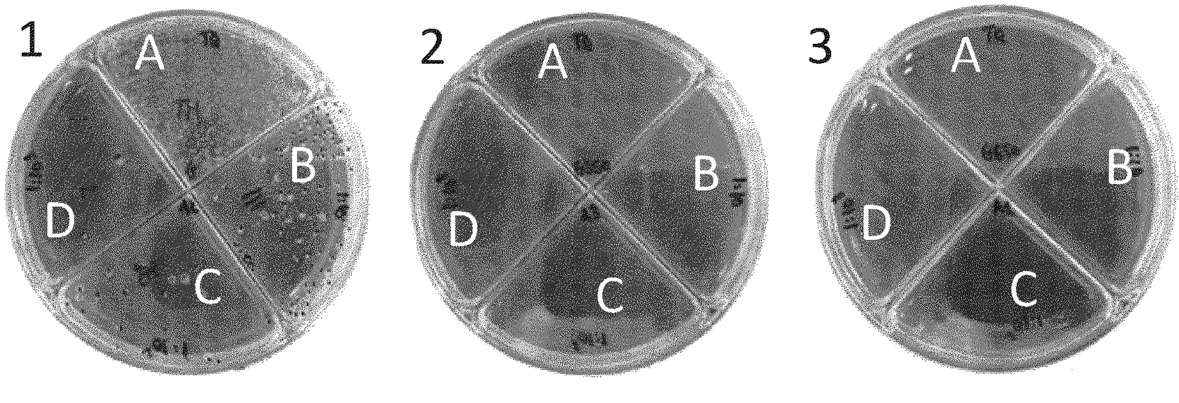

FIG. 19 shows the culture plates at the end of the antimicrobial experiments referred to: 1: CNT-SP of Example 35, 2: CNT-SP/Ag350 of Example 33, 3: CNT-SP/Ag650 of Example 34;

FIG. 20 shows a correlation graph between CFU counts and the Ag molar concentration of the suspensions;

FIG. 21 shows the culture plates at the end of the antimicrobial experiments referred to: 1: HSAG-SP of Example 38, 2: HSAG-SP/Ag350 of Example 36, 3: HSAG-SP/Ag650 of Example 37;

FIG. 22 shows a correlation graph between CFU counts and the Ag molar concentration of the suspensions;

FIG. 23 shows the culture plates at the end of the antimicrobial experiments referred to: 1: CB-SP of Example 41, 2: CB-SP/Ag350 of Example 39, 3: CB-SP/Ag650 of Example 40.

Figure 24:
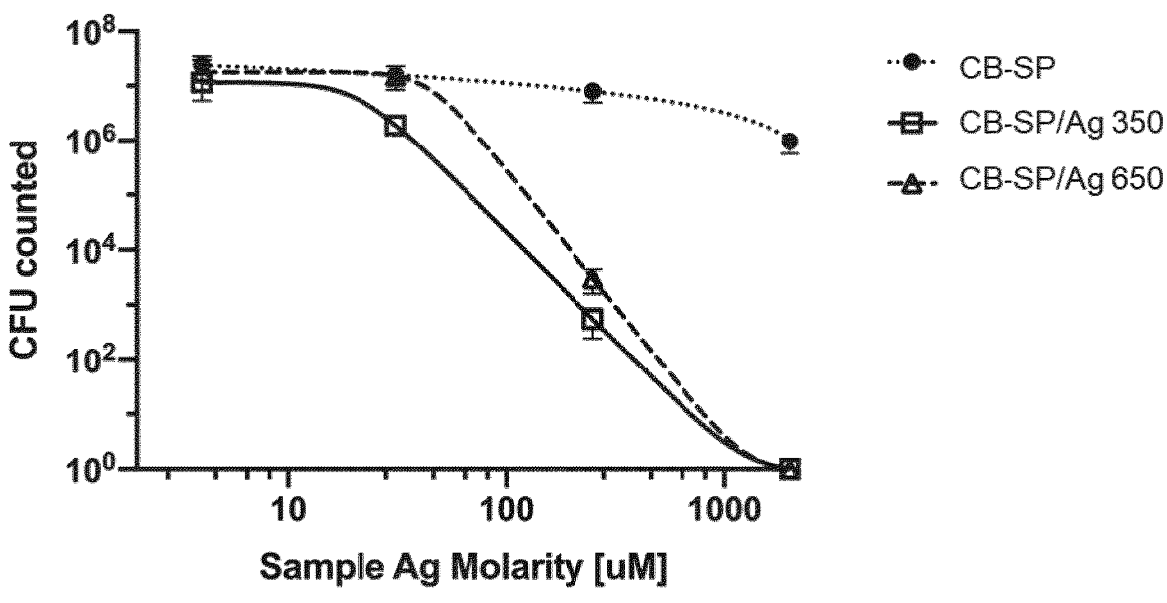
Figure 25:
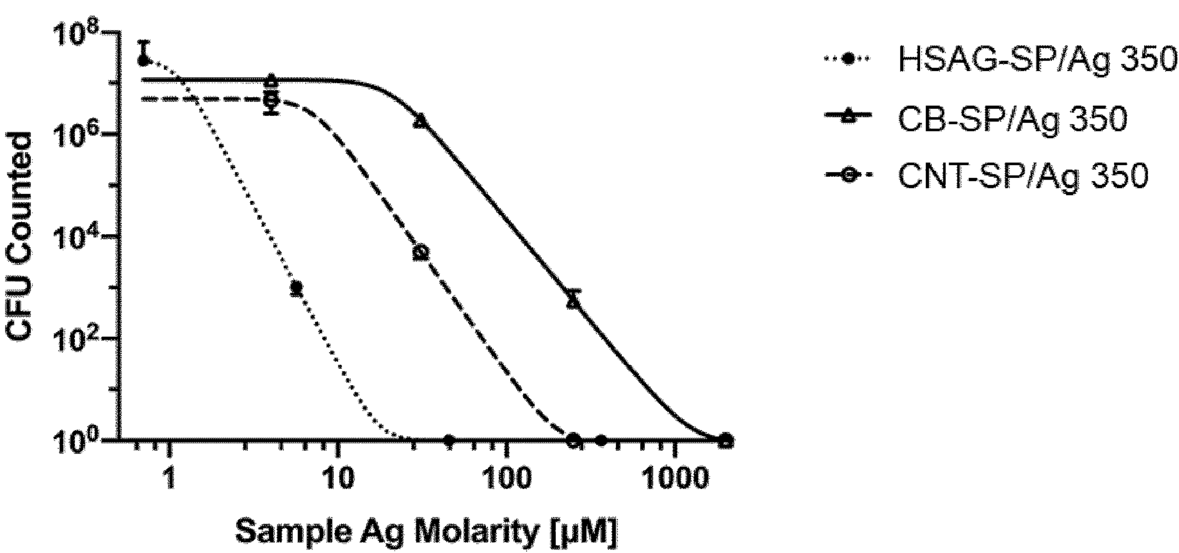
Figure 26:
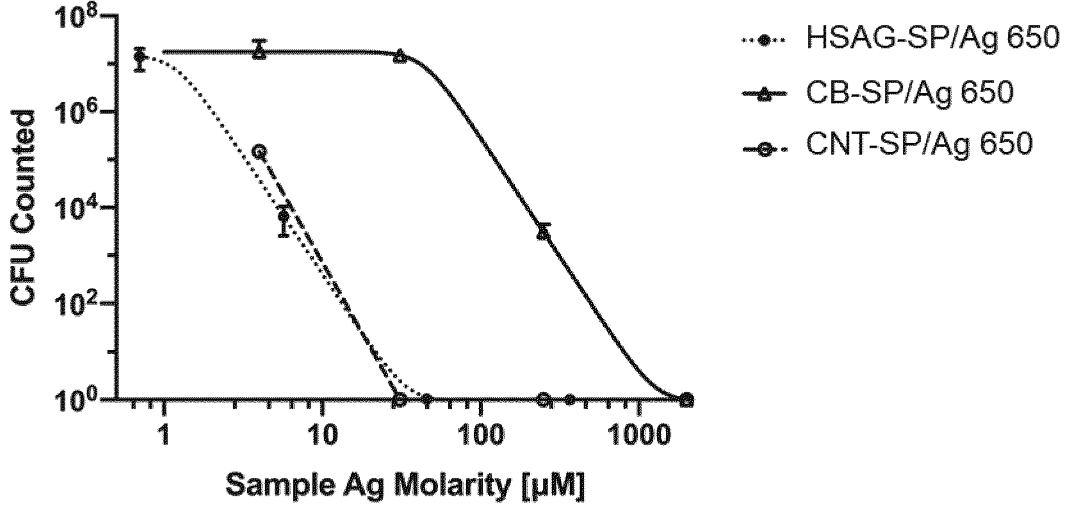

FIG. 24 shows a correlation graph between CFU counts and the Ag molar concentration of the suspensions;

FIG. 25 shows a correlation graph between CFU counts and the Ag molar concentration of the suspensions;

FIG. 26 shows a correlation graph between CFU counts and the Ag molar concentration of the suspensions.

MATERIALS

Reagents and solvents are commercially available and were used without any further purification: Serinol and isoserinol were kindly provided by Bracco. 2,5-hexandione, were purchased from Sigma-Aldrich.

Carbon Black N326 (CBN326) and N234 (CBN234) were from Cabot. Multiwall Carbon Nanotubes were NANOCYL® NC7000™ series, with carbon purity of 90%, average length of about 1.5 μm, BET surface area of 275 $m^2/g$, 316 ml of absorbed DBP/100 grams of CNT. High surface area graphite (HSAG) was Nano24 from Asbury Graphite Mills Inc., with carbon content reported in the technical data sheet of at least 99 wt %. Chemical composition determined from elemental analysis was, as wt %: carbon 99.5, hydrogen 0.4, nitrogen 0.1, oxygen<0.05. BET surface area was 330 $m^2/g$ and DBP absorption was 162 mL/100 g. Graphene Nanoplatelet (GnP) were from Sigma Aldrich.

Methods

Thermogravimetric Analysis

TGA tests under flowing $N_2$ (60 mL/min) were performed with a Mettler TGA SDTA/851 instrument according to the standard method IS09924-1. Samples (10 mg) were heated from 30 to 300° C. at 10° C./min, kept at 300° C. for 10 min, and then heated up to 550° C. at 20° C./min. After being maintained at 550° C. for 15 min, they were further heated up to 900° C. and kept at 900° C. for 30 min under flowing air (60 mL/min).

High-Resolution Transmission Electron Microscopy (HRTEM)

HRTEM investigations on HSAG samples were carried out with a Philips CM 200 field emission gun microscope operating at an accelerating voltage of 200 kV. Few drops of the suspensions were deposited on 200 mesh lacey carbon-coated copper grid and air-dried for several hours before analysis. During acquisition of HRTEM images, the samples did not undergo structural transformation. Low beam current densities and short acquisition times were adopted. To estimate the number of stacked graphene layers and the dimensions of the stacks visible in HRTEM micrographs, the Gatan Digital Micrograph software was used.

X-Ray Diffraction (XRD)

Wide angle X-ray Diffraction patterns were obtained in reflection, with an automatic Bruker D8 Advance diffractometer, with nickel filtered Cu-$K_\alpha$ radiation. Patterns were recorded in 4°-80° as the 2θ range, being 2θ the peak diffraction angle. Distance between crystallographic planes of HSAG was calculated from the Bragg law. The $D_{hk\ell}$ correlation length, in the direction perpendicular to the hkl crystal graphitic planes, was determined applying the Scherrer equation:

$$D_{hk\ell}=K\lambda/(\beta_{hk\ell}\cos\theta_{hk\ell}) \quad (1)$$

where K is the Scherrer constant, λ is the wavelength of the irradiating beam (1.5419 Å, Cu-$K_\alpha$), $\beta_{hk\ell}$ is the width at half height, and $\theta_{hk\ell}$ is the diffraction angle. The instrumental broadening, b, was determined by obtaining a XRD pattern of a standard silicon powder 325 mesh (99%), under the same experimental conditions. The width at half height $\beta_{hk\ell}=(\beta_{hk\ell}-b)$ was corrected, for each observed reflection with $\beta_{hk\ell}<1°$, by subtracting the instrumental broadening of the closest silicon reflection from the experimental width at half height, $B_{hk\ell}$.

Biological Assay

Antimicrobial properties of CA-SP/Ag adducts were tested against *Escherichia coli* JM109 (*E. coli*, Gram-negative bacterial strain).

Figure 1:
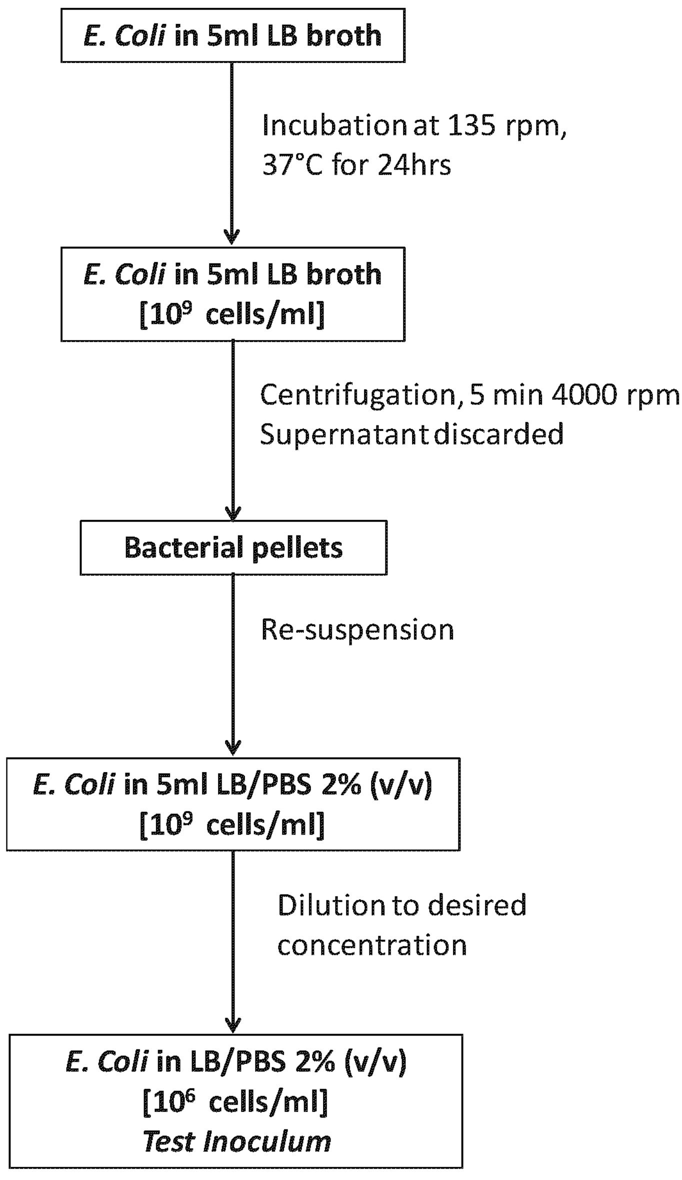
FIG. 1 shows a flowchart of the preparation of the Test Inoculum.

Preparation of test inoculum (bacteria suspension). The procedure is schematically presented in FIG. 1.

Bacteria were pre-cultured in 5 mL of Luria-Bertani (LB) broth at 37° C. under shaking at 135 rpm for 20 hrs, until reaching an OD at λ=600 nm ($OD_{600\ nm}$)≈1, approximately corresponding to $10^9$ bacteria/mL. Afterwards, the bacterial suspension was centrifuged for 5 min at 4,000 rpm, the supernatant discarded, and bacterial pellet was then resuspended in 5 mL of 2% (v/v) LB in PBS. Next, the bacterial suspension was diluted to reach the desired microbial concentration of $10^6$ bacteria/mL. The final suspension is hereinafter referred to as test inoculum.

Figure 2:
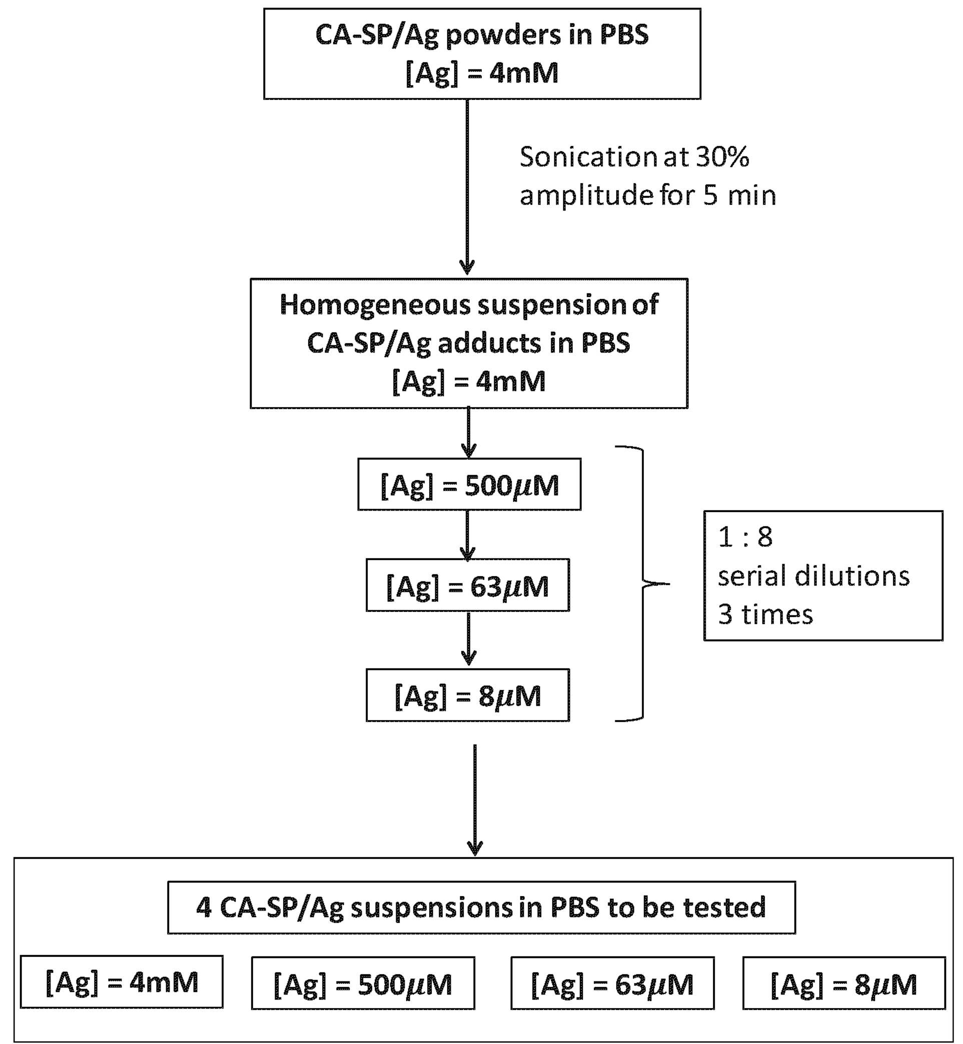
FIG. 2 shows a flowchart of the preparation of suspensions of CA-SP/Ag adducts.

Preparation of adducts' suspensions. The procedure is schematically presented in FIG. 2. Each adduct was dispersed in 4 mL of PBS to obtain the Ag concentration [Ag] equal to 4 mM. As a matter of comparison, suspensions of carbon allotropes' adducts with SP (G-SP, CB-SP and CNT-SP) were prepared at the same SP concentration used for CA-SP/Ag350 adducts. The suspensions of either CA-SP or CA-SP/Ag were sonicated for 5 min at 30% amplitude, by using a Tip Sonicator Hielscher Ultrasonic UP200S. The test suspensions were finally obtained by diluting the above reported 4 mM [Ag] suspension to achieve a final [Ag] of 500 μM, 63 μM, 8 μM. The suspensions of the CA-SP adducts were diluted analogously, in order to obtain suspensions with the same SP concentration as in CA-SP/Ag counterparts. The mother suspension with 4 mM Ag concentration was tested as well.

Figure 3:
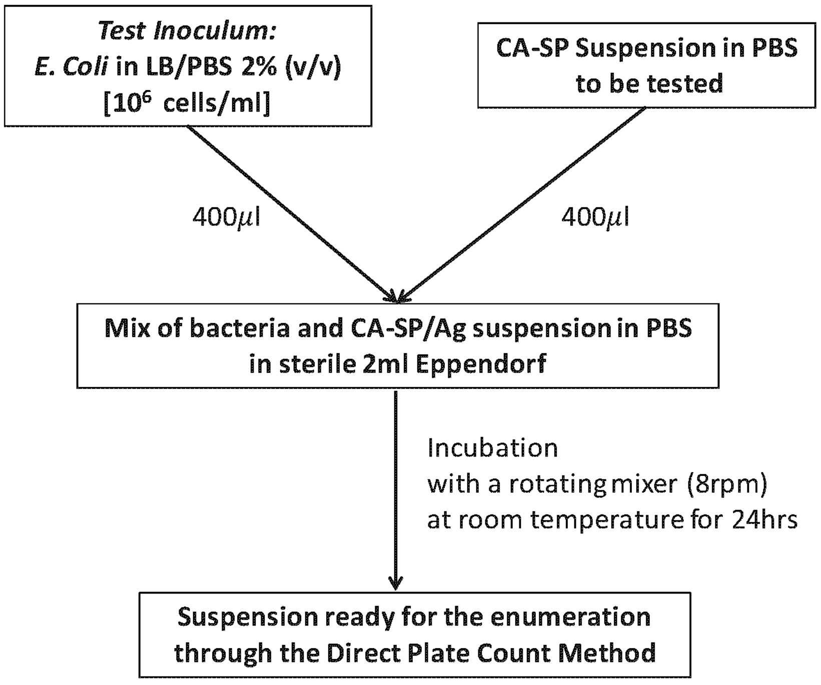
FIG. 3 shows a flowchart of the antimicrobial tests.

Antibacterial tests. The procedure is schematically presented in FIG. 3.

For antibacterial tests, 400 μL of each test suspension were mixed with 400 μL of test inoculum suspension in 2 mL polypropylene test tubes and subsequently incubated at room temperature for 24 hrs. In order to avoid precipitation, the suspensions were kept under rotation (8 rpm) with a rotating mixer with rotisseries. Bacterial suspensions cultured in PBS were used as a comparative test, negative control ($CTRL^-$, i.e., viable control, no antibacterial activity), while aqueous bacterial suspensions inoculated with 50

μM $AgNO_3$ were used as a further comparative test, positive control ($CTRL^+$). After 24-hrs incubation under rotation, the number of viable bacteria was determined by means of the direct plate count method.

Figure 4:
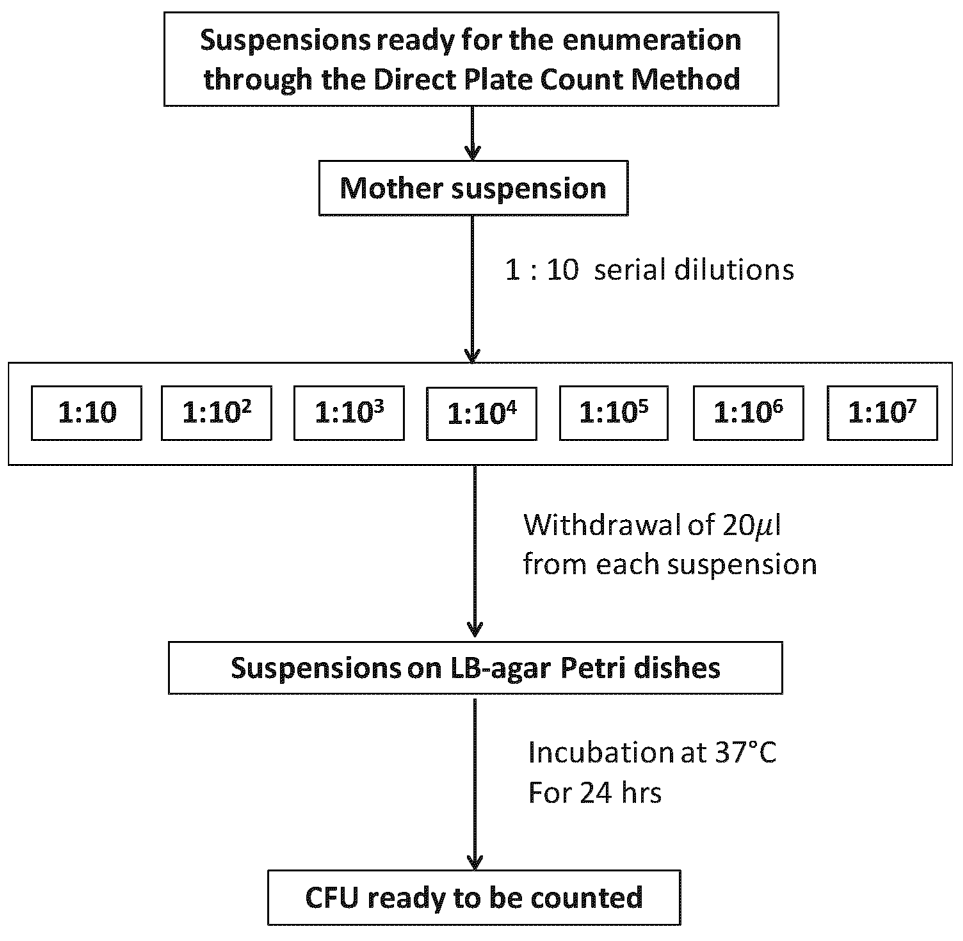
FIG. 4 shows a flowchart of the Direct Plate Count Method.

Direct plate count method. The procedure is schematically presented in FIG. 4.

The suspensions taken from the rotating mixer were diluted: 10 μL of each of these suspensions were diluted with 90 μL of LB broth. 10 μL of the resulting suspension were diluted with 90 μL of LB broth. The total number of dilutions was 7. The concentration of the final suspension was $1/10^7$ with respect to the concentration of the suspension taken from the rotating mixer. 20 μL of the final suspensions were poured in LB-agar Petri dishes and incubated for 24 hours at 37° C. After such incubation, the number of colony forming units (CFUs) was visually inspected and counted.

EXAMPLES

In the Examples 1-6 is described the preparation of adducts between pyrrole compounds (PyC) and $sp^2$ hybridized carbon allotropes (CA): CA-PyC.

| Example | $sp^2$ carbon allotrope | PyC |
|---|---|---|
| 1 | multi-walled carbon nanotubes (CNT) | SP |
| 2 | graphene nanoplatelets (GnP) | SP |
| 3 | high surface area graphite (HSAG) | SP |
| 4 | carbon black CB N326 | SP |
| 5 | carbon black CB N234 | SP |
| 6 | high surface area graphite | iso-SP |

Examples 1-6: Preparation of Adducts Between Pyrrole Compounds (PyC) and $Sp^2$ Hybridized Carbon Allotropes (CA): CA-PyC Adducts

Example 1: Adduct Between Multi-Walled Carbon Nanotubes (CNT) and 2-(2,5-dimethyl-1H-pyrrol-1-yl)propan-1,3-diol (SP)-CNT-SP In a 50 mL flask, equipped with magnetic stirrer, CNT (200 mg, 2.8 mmol) and acetone (15 mL) were sequentially added. The thus obtained suspension was sonicated for 15 minutes using a 2 L ultrasound water bath. Afterwards, a solution of 2-(2,5-dimethyl-1H-pyrrol-1-yl)propan-1,3-diol (10% mol/mol, 0.28 mmol) in acetone (25 mL) is added to the suspension. The mixture was then sonicated for 15 minutes. Afterwards, the acetone was removed under reduced pressure using a rotavapor. The black powder thus obtained was placed in a 100 mL flask and heated to 180° C. for 2 h. The adduct was then transferred in a Büchner filter and repeatedly washed with acetone (3×100 mL).

Example 2: Adduct Between Graphene Nanoplatelets (GnP) and 2-(2,5-dimethyl-1H-pyrrol-1-yl)propan-1,3-diol (SP)-GnP-SP GnP-SP was prepared with the procedure described in example 1, using graphene nanoplatelets instead of CNT.

Example 3: Adduct Between High Surface Area Graphite (HSAG) and 2-(2,5-dimethyl-1H-pyrrol-1-yl)propan-1,3-diol (SP)-HSAG-SP HSAG-SP was prepared with the procedure described in example 1, using high surface area graphite instead of CNT.

Example 4: Adduct Between Carbon Black (CBN326) and 2-(2,5-dimethyl-1H-pyrrol-1-yl)propan-1,3-diol (SP)-CBN326-SP CBN326-SP was prepared with the procedure described in example 1, using carbon black CBN326 instead of CNT.

Example 5: Adduct Between Carbon Black (CBN234) and 2-(2,5-dimethyl-1H-pyrrol-1-yl)propan-1,3-diol (SP)-CBN234-SP CBN234-SP was prepared with the procedure described in example 1, using carbon black CBN234 instead of CNT.

Example 6: Adduct Between High Surface Area Graphite (HSAG) and 3-(2,5-dimethyl-1H-pyrrol-1-yl)propan-1,2-diol (iSP)-HSAG-iSP HSAG-iSP was prepared with the procedure described in example 1, using 3-(2,5-dimethyl-1H-pyrrol-1-yl)propan-1,2-diol instead of SP.

Characterization of CA-PyC Adducts from Examples 1-6.

Characterization was performed by means of TGA, XRD, HRTEM analyses.

In Table 1, are shown the results of TGA analysis of the pristine $sp^2$ carbon allotropes and of the adducts between PyC and the $sp^2$ carbon allotropes (CA-PyC). The samples of CA-PyC adducts are from examples 1-6.

Figure 5:
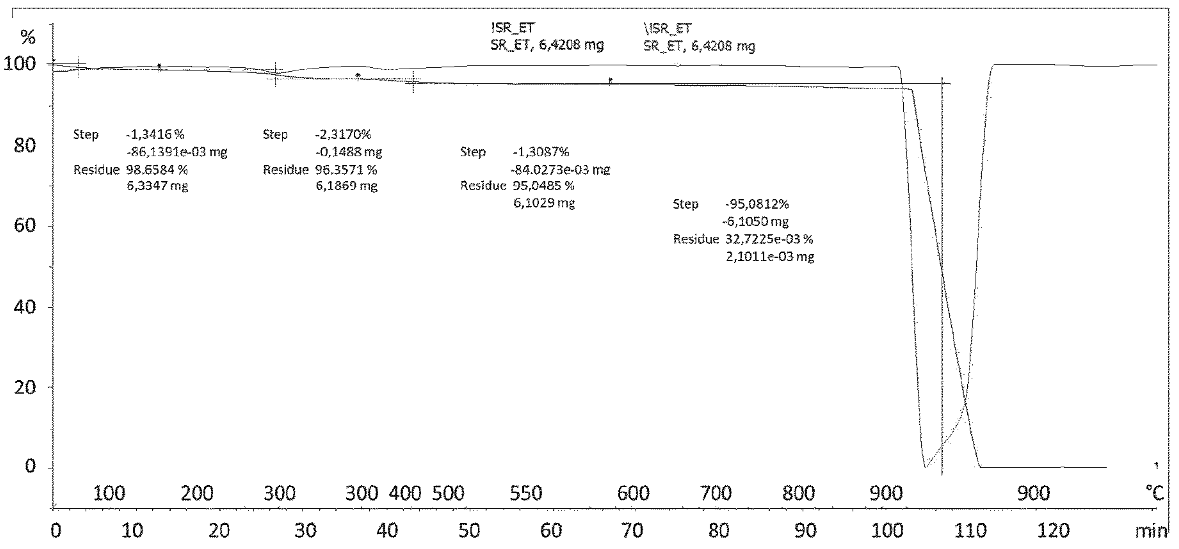
FIG. 5 shows the TGA graph for the sample CNT-SP of the composition according to Example 4.
Figure 6:
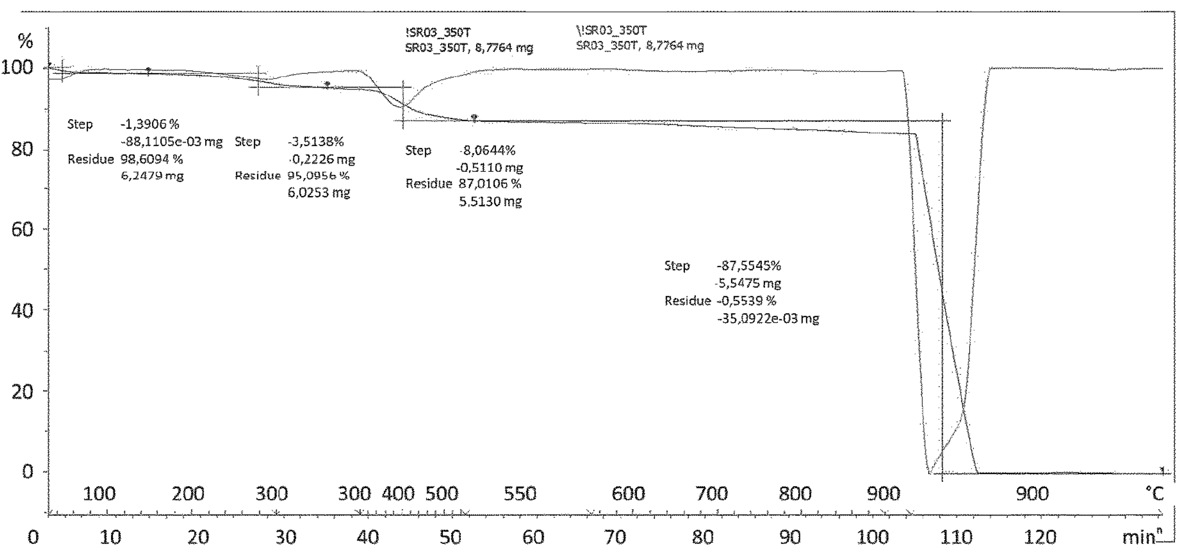
FIG. 6 shows the TGA graph for the sample HSAG-SP of the composition according to Example 3.
Figure 7:
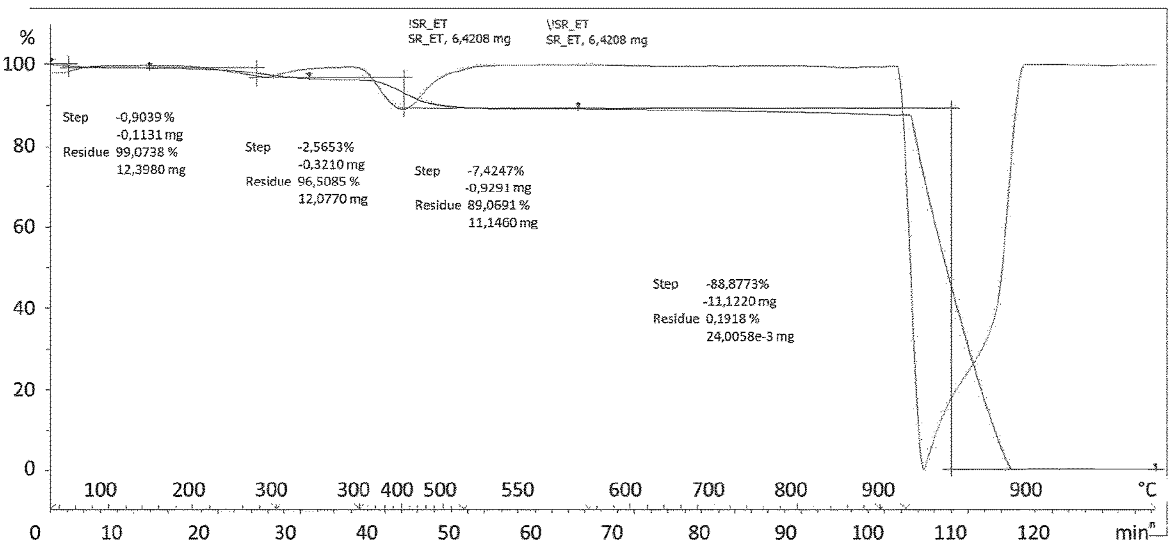
FIG. 7 shows the TGA graph for the sample CBN326-SP of the composition according to Example 4.

In FIGS. 5, 6, 7 are shown the TGA thermograms of the samples from Examples 1, 3, 4, respectively.

TABLE 1

Mass losses (mass %) for pristine carbon allotropes and for CA-PyC adducts, from TGA analyses, and values of PyC phc in the adducts

| | | Temperature (° C.) range | | | | | |
|---|---|---|---|---|---|---|---|
| Example | Sample | 0 < T < 200 | 200 < T < 700 | 700 < T < 900 | T > 900 | Residue | PyC (phc) |
| / | CNT | 0.8 | 1.6 | 0.1 | 97.5 | 0 | 0 |
| 1 | CNT-SP | 1.3 | 3.6 | 2 | 93.1 | 0 | 4.2 |
| / | GnP | 0.2 | 1.3 | 1 | 97.5 | 0 | 0 |
| 2 | GnP-SP | 0.2 | 5 | 3 | 91.8 | 0 | 6.1 |
| / | HSAG | 0.6 | 3 | 1 | 89.8 | 0 | 0 |
| 3 | HSAG-SP | 1.3 | 12.5 | 3 | 83.2 | 0 | 13.8 |
| / | CBN326 | 0.6 | 1 | 1 | 97.4 | 0 | 0 |
| 4 | CBN326-SP | 1 | 10 | 2 | 87 | 0 | 11.5 |
| / | CBN234 | 0.5 | 1 | 1 | 97.5 | 0 | 0 |
| 5 | CBN234-SP | 1.4 | 7 | 3.7 | 87.9 | 0 | 9.9 |
| 6 | HSAG-iSP | 2 | 13 | 3 | 82 | 0 | 14.6 |

TGA thermograms of Samples from Examples 1, 3, 4 are in FIGS. 5-7.

The mass loss below 200° C. can be attributed to low molar mass substances, absorbed on CA surface, mainly water.

In the case of pristine CA, the mass loss between 150° C. and 900° C. could be mainly ascribed to alkenylic defects of CA.

The mass loss due to SP bonded to CA was calculated moving from the mass loss in the temperature range from 200 to 900° C.

The carbonaceous residual was then completely burned for temperatures higher than 900° C.

Quantitative data from TGA analyses of Samples from Examples 1, 2, 3, 4, 5, 6 are in Table 1.

The relative amount with respect to CA of the functionalizing molecule is expressed with the measure unit phc.

Definition and Calculation of Phc phc means per hundred carbon, i.e. the mass of substance other than CA per hundred grams of CA.

The measure unit "phc" refers mainly to PyC.

phc is calculated through the following Equation, Equation 1:

$$phc = \frac{\%\ \text{mass loss}^{CA\text{-}SP\ washed}_{200^\circ C.\rightarrow 900^\circ C.} - \%\ \text{mass loss}^{CA\ Pristine}_{200^\circ C.\rightarrow 900^\circ C.}}{\%\ \text{mass loss}^{CA\ Pristine}_{900^\circ C.\rightarrow}} \cdot 100 \qquad \text{Equation 1}$$

Results from XRD and HRTEM analyses of CA and CA-SP samples are discussed below in the text together with the results of CA-SP/Ag adducts.

Examples 7-18. Invention. Preparation of Adducts of Silver (Ag) Nanoparticles (NPs) with CA-PyC Adducts: CA-PyC/Ag Adducts Objective of the Examples 7-18 was the preparation of adducts of CA-SP with Ag particles. Indeed, in the Examples 7-18 is described the preparation of adducts of silver (Ag) nanoparticles (NPs) with CA-PyC adducts: CA-PyC/Ag. In all these examples, Ag particles were formed in situ through the reduction of a silver salt. Reducing agent were not added to the reaction mixture. The CA-SP adduct was used as obtained, without further modification.

Example 7: Preparation of the Adduct Between Cnt-Sp and Silver (Cnt-Sp/Ag 350) (Tollens' Reagent 350 μL)

Tollens' reagent was prepared as follows: 1 mL of a 0.6 M $AgNO_3$ solution and 1 mL of a 2.8 M NaOH solution in distilled water ($dH_2O$) were mixed in a glass vial causing the formation of a brown precipitate, thus, $NH_4OH$ was added dropwise until a complete precipitate dissolution was achieved.

In a 15 mL falcon conical centrifuge tube, CNT-SP (250 mg) and $H_2O$ (5 mL) were sequentially added. The so obtained suspension was sonicated for 10 minutes using a 2 L ultrasound water bath. Afterwards, 350 μL of Tollens' reagent were added to the suspension. The mixture was then brought to volume (final volume: 7 mL) with distilled $H_2O$ and centrifuged (Refrigerated Centrifuge 3-16PK, Sigma Laborzentrifugen) at 4,000 rpm for 15 minutes (3×10 mL $H_2O$). The supernatant was removed and the black powder was dried.

Example 8: Preparation of the Adduct Between CNT-SP and Silver (CNT-SP/Ag 650) (Tollens' Reagent 650 μL)

CNT-SP/Ag 650 was prepared with the procedure described in example 7, using 650 μL of Tollens' reagent.

Example 9: Preparation of the Adduct Between GnP-SP and Silver (GnP-SP/Ag 350) (Tollens' reagent 350 μL)

GnP-SP/Ag 350 was prepared with the procedure described in example 7, using GnP-SP instead of CNT-SP and 350 μL of Tollens' reagent.

Example 10: Preparation of the Adduct Between GnP-SP and Silver (GnP-SP/Ag 650) (Tollens' Reagent 650 μL)

GnP-SP/Ag 650 was prepared with the procedure described in example 7, using GnP-SP instead of CNT-SP and 650 μL of Tollens' reagent.

Example 11: Preparation of the Adduct Between HSAG-SP and Silver (HSAG-SP/Ag 350) (Tollens' Reagent 350 μL)

HSAG-SP/Ag 350 was prepared with the procedure described in example 7, using HSAG-SP instead of CNT-SP and 350 μL of Tollens' reagent.

Example 12: Preparation of the Adduct Between HSAG-SP and Silver (HSAG-SP/Ag 650) (Tollens' Reagent 650 μL)

HSAG-SP/Ag 650 was prepared with the procedure described in example 7, using HSAG-SP instead of CNT-SP and 650 μL of Tollens' reagent.

Example 13: Preparation of the Adduct Between CBN326-SP and Silver (CBN326-SP/Ag 350) (Tollens' Reagent 350 μL)

CBN326-SP/Ag 350 was prepared with the procedure described in example 7, using CBN326-SP instead of CNT-SP and 350 μL of Tollens' reagent.

Example 14: Preparation of the Adduct Between CBN326-SP and Silver (CBN326-SP/Ag 650) (Tollens' Reagent 650 μL)

CBN326-SP/Ag 650 was prepared with the procedure described in example 7, using CBN326-SP instead of CNT-SP and 650 μL of Tollens' reagent.

Example 15: Preparation of the Adduct Between CBN234-SP and Silver (CBN234-SP/Ag 350) (Tollens' Reagent 350 μL)

CBN234-SP/Ag 350 was prepared with the procedure described in example 7, using CBN234-SP instead of CNT-SP and 350 μL of Tollens' reagent.

Example 16: Preparation of the Adduct Between CBN234-SP and Silver (CBN234-SP/Ag 650) (Tollens' Reagent 650 μL)

CBN234-SP/Ag 650 was prepared with the procedure described in example 7, using CBN234-SP instead of CNT-SP and 650 μL of Tollens' reagent.

Example 17: Preparation of the Adduct Between HSAG-iSP and Silver (HSAG-iSP/Ag 350) (Tollens' Reagent 350 μL)

HSAG-iSP/Ag 350 was prepared with the procedure described in example 7, using HSAG-iSP instead of CNT-SP and 350 μL of Tollens' reagent.

Example 18: Preparation of the Adduct Between HSAG-iSP and Silver (HSAG-iSP/Ag 650) (Tollens' Reagent 650 μL)

HSAG-iSP/Ag 650 was prepared with the procedure described in example 7, using HSAG-iSP instead of CNT-SP and 650 μL of Tollens' reagent.

Characterization of Adducts of Silver (Ag) Nanoparticles (NPs) with CA-PyC Adducts, CA-PyC/Ag Adducts, from Examples 7-18.

Characterization was performed by means of TGA, XRD, HRTEM analyses.

In particular, characterization in order to verify the formation of $Ag^0$, was performed by means of X-ray diffraction and high resolution transmission electron microscopy.

Figure 8:
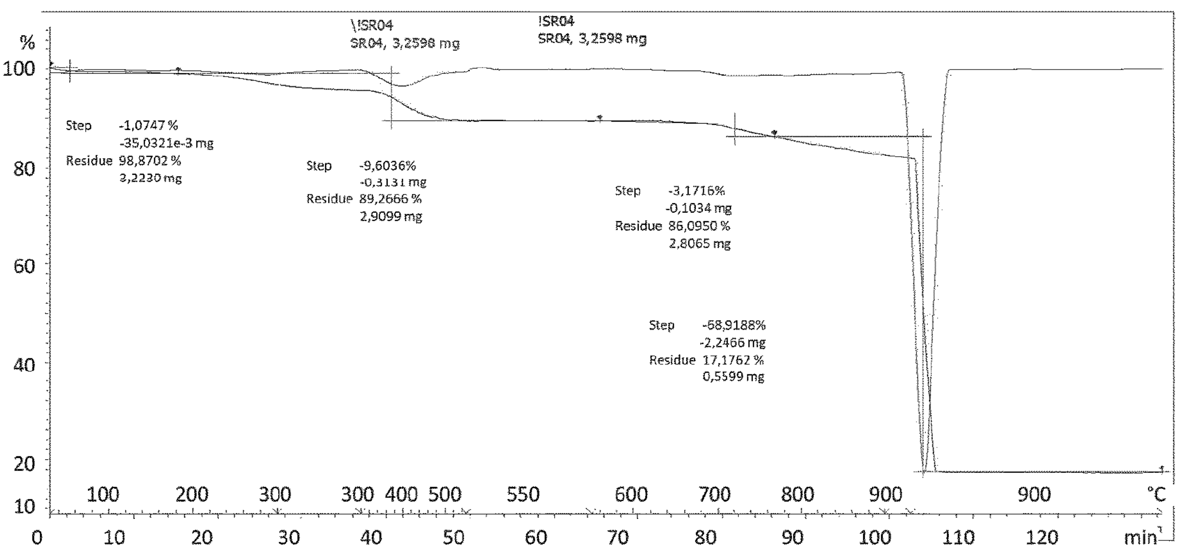
FIG. 8 shows the TGA graph for the sample CNT-SP/Ag 350 of the composition according to Example 7.
Figure 9:
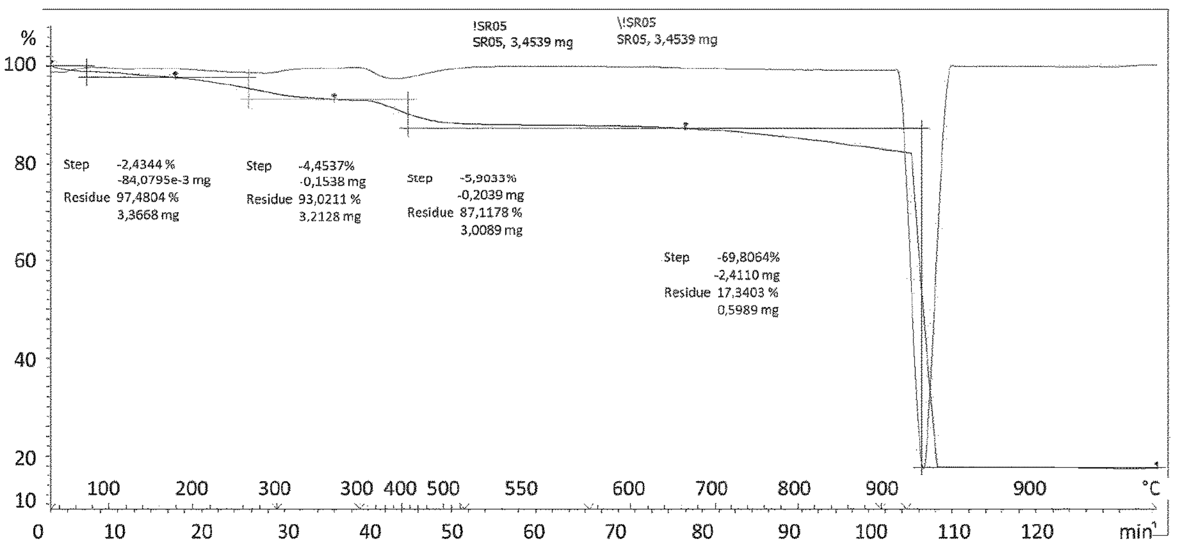
FIG. 9 shows the TGA graph for the sample CNT-SP/Ag 650 of the composition according to Example 8.
Figure 10:
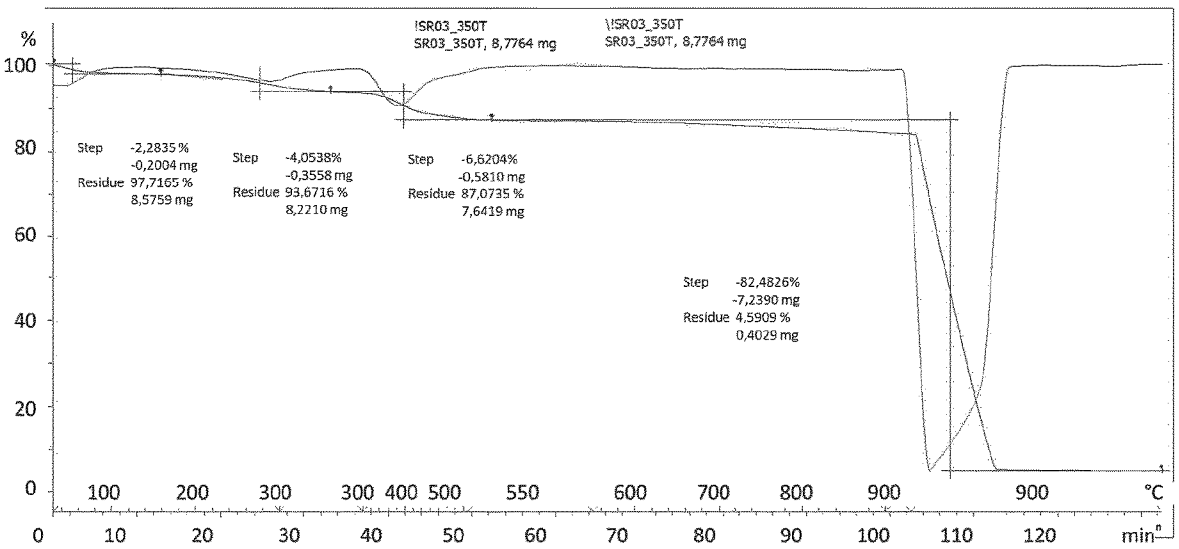
FIG. 10 shows the TGA graph for the sample HSAG-SP/Ag 350 of the composition according to Example 11.
Figure 11:
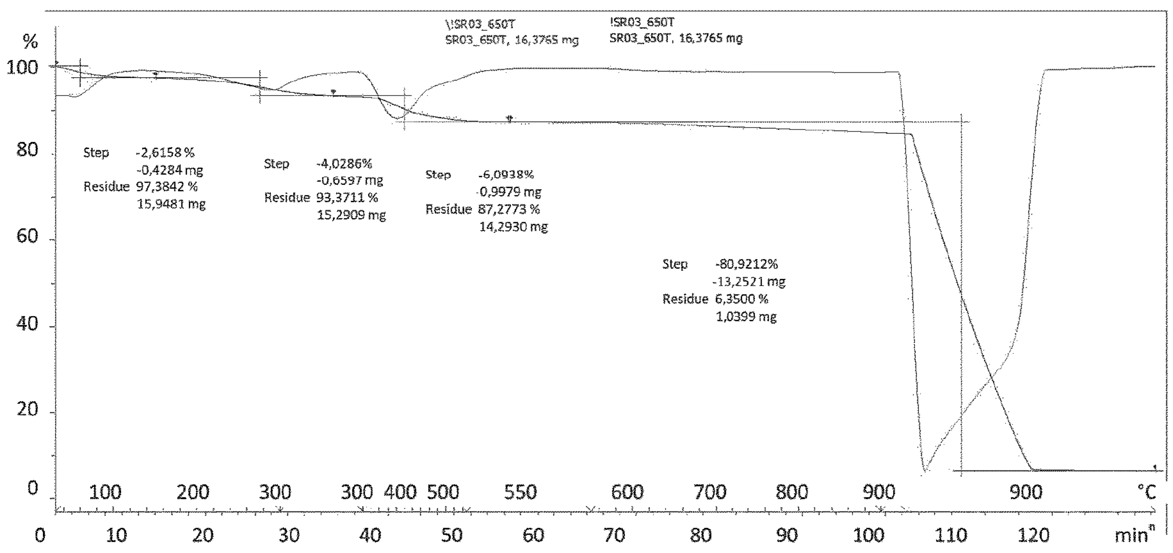
FIG. 11 shows the TGA graph for the sample HSAG-SP/Ag 650 of the composition according to Example 12.
Figure 12:
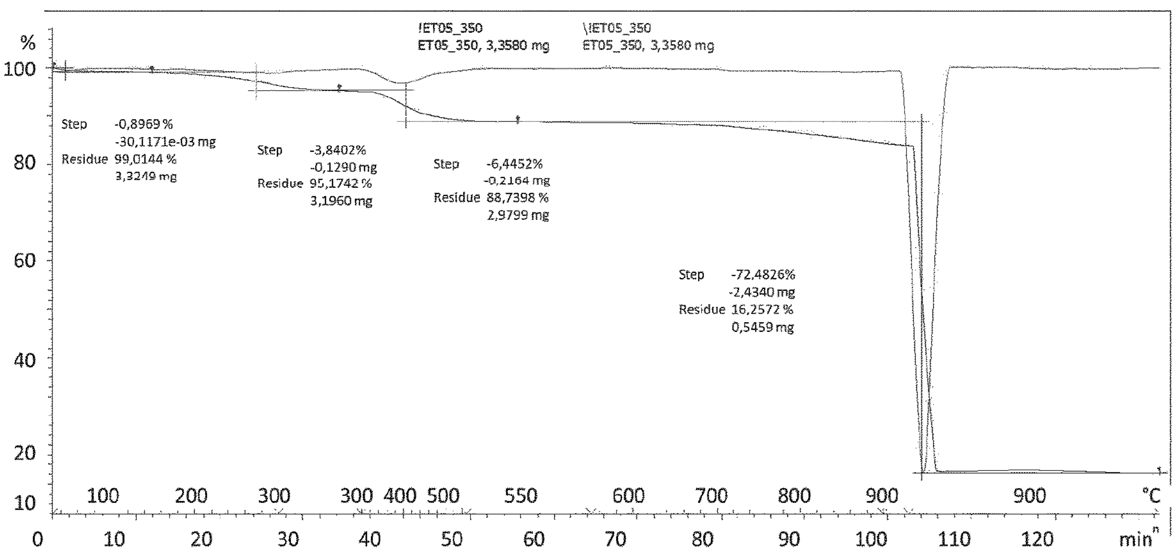
FIG. 12 shows the TGA graph for the sample CBN326-SP/Ag 350 of the composition according to Example 13.
Figure 13:
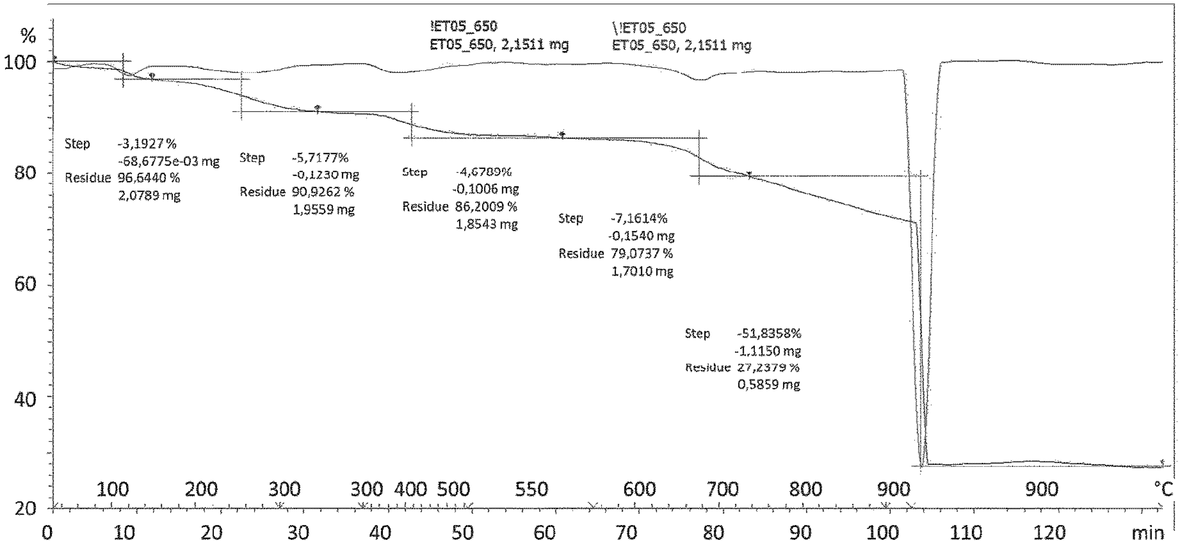
FIG. 13 shows the TGA graph for the sample CBN326-SP/Ag 650 of the composition according to Example 14.

In Table 2, are reported the results of TGA analysis of the CA-PyC/Ag adducts. The samples are from examples 7, 8, 11, 12, 13, 14. In FIG. 8, 9, 10, 11, 12, 13 are the thermograms of TGA analysis of adducts from examples 7, 8, 11, 12, 13, 14, respectively.

TABLE 2

Mass losses (mass %) for CA-PyC/Ag adducts, from TGA analyses.

| | | Temperature range | | | | |
|---|---|---|---|---|---|---|
| Example | Sample | 0 < T < 200° C. | 200 < T < 700° C. | 700 < T < 900 ° C. | T > 900° C. | residue |
| 7 | CNT-SP/ Ag 350 | 1 | 9.6 | 3.2 | 69 | 17.2 |
| 8 | CNT-SP/ Ag 650 | 2.3 | 4.4 | 6 | 70 | 17.3 |
| 11 | HSAG-SP/ Ag 350 | 2.2 | 4.1 | 6.6 | 82.5 | 4.6 |
| 12 | HSAG-SP/ Ag 650 | 2.5 | 4 | 6 | 81 | 6.5 |
| 13 | CBN326-SP/ Ag 350 | 1 | 3.8 | 6.4 | 72.5 | 16.3 |
| 14 | CBN326-SP/ Ag 650 | 3.2 | 10.4 | 7 | 53 | 26.4 |

The interpretation of TGA results been reported above, Moreover, the amount of Ag in the adduct is documented and could be calculated from the value of the residue.

In Table 2 are the quantitative data from TGA analysis.

XRD Analysis

Results from XRD analysis are discussed in the following for CA, CA-SP, CA-SP/Ag samples.

The XRD analysis is diagnostic for assessing the presence of Ag nanoparticles in CA-PyC/Ag adducts. Indeed, in this case, the typical reflections of $Ag^0$ are visible in the XRD pattern.

In FIG. 14, the XRD patterns of the following substances are reported.

| | | |
|---|---|---|
| FIG. 14A | HSAG | (a) |
| | HSAG-SP | (b) |
| | HSAG-SP/Ag 350 | (c) |
| | HSAG-SP/Ag 650 | (d) |
| FIG. 14B | CNT | (a) |
| | CNT-SP | (b) |
| | CNT-SP/Ag 350 | (c) |
| | CNT-SP/Ag 650 | (d) |
| FIG. 14C | CB N326 | (a) |
| | CBN326-SP | (b) |
| | CBN326-SP/Ag 350 | (c) |
| | CBN326-SP/Ag 650 | (d) |

Pristine HSAG, CNT and CB N326

In pristine HSAG, CNT and CB N326, crystalline order in the direction orthogonal to structural layers is revealed by (002) reflection at 26.6°, which corresponds to an interlayer distance, obtained from the Bragg's law, of 0.338 and 0.350 nm for HSAG and CNT respectively. These interlayer distances are slightly larger than the one of ordered graphite samples ($d_{002}$=0.335 nm). The in-plane order is shown by 100 and 110 reflections, at 42.5° and 77.6° respectively.

In pristine HSAG (FIG. 14Aa) and CNT samples (FIG. 14 Ba), by applying the Scherrer equation to (002) and (110) reflections, respectively, the out-of-plane (D⊥) and the in-plane ($D_{||}$) correlation lengths were calculated. From the values of (D⊥) and of the interlayer distance, the number of stacked layers was estimated to be about 35 for Graphite Nano 307 (HSAG) and 12 for CNT. In particular, for HSAG, values were 9.8 nm for (D⊥) and 30.2 nm for ($D_{||}$). The in-plane correlation length is thus larger than the out-of-plane correlation length.

Adducts of CA with SP and Adducts of CA/SP with Ag Nanoparticles

The number of stacked layers in HSAG-SP was calculated by applying the Scherrer equation to 002 reflection. From the calculation HSAG-SP, HSAG-SP/Ag 350 and HSAG-SP/Ag 650 samples show 21, 19 and 19 stacked layers respectively. Reflections due to in plane order are visible also in the patterns of HSAG-SP, HSAG-SP/Ag 350 and HSAG-SP/Ag 650. These experimental findings demonstrate that the functionalization procedure leads to exfoliate the graphitic aggregate and does not alter the bluk structure of HSAG.

The number of stacked layers in CNT-SP, CNT-SP/Ag 350 and CNT-SP/Ag 650 samples was calculated by applying the Scherrer equation to 002 reflection. All the CNT based samples show the same number of stacked crystalline layers, as expected (12, as reported above).

Patterns of carbon black samples present broad 002 reflections. The out-of-plane correlation lengths (D⊥) were estimated, by applying the Scherrer equation, to be about 1.9 nm which corresponds to a number of layers stacked in crystalline domain of about 5. Low intensity can be observed for the broad reflections characteristics of the order inside the graphitic planes. In all samples, 101 and 112 reflections are negligible. The absence of (hkℓ) reflections with ℓ≠0, other than (002), is a clear indication of the structural disorder of CB.

FIGS. 14Ac, 14Ad, 14Bc, 14Bd, 14Cc and 14Cd report the XRD patterns of HSAG-SP/Ag 350, HSAG-SP/Ag 650, CNT-SP/Ag 350, CNT-SP/Ag 650, CBN326-SP/Ag 350 and CBN326-SP/Ag 650 samples. All patterns reported shows the diffraction peaks at 38.24°, 44.27°, 64.59° and 77.500 corresponding to the (111), (200), (220) and (311) facets of the Ag. These results of the XRD investigation indicate that $Ag^0$ particles are present in the CA-SP/Ag adduct.

High Resolution Transmission Electron Microscopy (HR-TEM) Analysis

Results from HRTEM analysis are discussed in the following for CA, CA-SP, CA-SP/Ag samples.

In FIG. 15-17 are shown micrographs of adducts of CA-SP adduct with Ag particles.

What is shown in the Figures is in the following Table.

| | |
|---|---|
| FIG. 15 | HSAG-SP/Ag 650 |
| FIG. 16 | CBN326-SP/Ag 650 |
| FIG. 17 | CNT-SP/Ag 650 |

In FIG. 15 (B), arrow indicates graphitic aggregates, i.e. several graphene layers parallelly stacked onto each other. In FIG. 15 (B), Arrow 3 indicates graphene nanoplatelets. Stacked layers form 4-23 nm thick structures (FIG. 15 B). Assuming a theoretical 0.34 nm distance between each graphene layer, it is possible to infer that the number of graphene layers composing our graphite samples approximately ranges from 10 to 70. This theoretical distance of 0.34 nm was almost identical to the experimental 0.32 nm interplanar spacing resulted from the software analysis carried out through the software Gatan Microscopy Suite. These findings led to hypothesize that the original interplanar spacing was not altered after the functionalization process, thus oxygenation of graphite samples occurred predominantly in peripheral positions, essentially on the edges.

In FIGS. 15B-D, it can be seen that Ag NPs are homogeneously dispersed in the HSAG-SP/Ag 650 sample. The size of the spherical NPs is from 12 Å to 50 nm with the average size about 50 Å. A large aggregate of Ag NPs is indicated in FIG. 15 (B) by arrow 2 and in FIG. 15(C) by arrow 5. A large aggregate of AgNPs is also visible in FIG. 15 (D), indicated by arrow 5. Arrow 4 in FIG. 15 (C) and arrow 6 in FIG. 15 (D) indicate small spherical Ag NPs.

CBN326-SP/Ag 650

FIG. 16 shows HRTEM micrographs for the sample CB-SP/Ag 650. Scalebar: (A) 500 nm, (B) 50 nm, (C) 20 nm.

Microscopical agglomerates are in (FIG. 16 B), indicated by arrow 1. Peculiar spherical structures of CB can be observed at higher magnifications (FIG. 16 C, D), resulting in 42±6 nm diameter acini.

In FIG. 16D, it can be seen the decoration of CB particles by Ag nanoparticles. The Ag nanoparticles, indicated by arrow 2 and arrow 3, are homogeneously dispersed in the CBN326-SP/Ag 650 sample. The size of the spherical nanoparticles is from 20 Å to 50 nm with the average size about 25 Å.

FIG. 16—HRTEM micrographs for sample CBN326-SP/Ag 650. (A) Diffraction pattern. (B) Scalebar: 500 nm. (C), (D)—Scalebar: 50 nm and 20 nm respectively CNT/SP-Ag FIG. 17 shows HRTEM micrographs for the sample CNT-SP/Ag 650. Scalebar: (A) 100 nm, (B) 50 nm, (C) 5 nm.

Bundles of filaments are indicated in FIG. 17B by arrow 1. The diameter of a single nanotube ranges from 5 to 9 nm (FIG. 17 C), with a mean value of 7±1 nm. In FIGS. 17B-D, it can be seen that Ag nanoparticles are homogeneously dispersed in the CNT-SP/Ag 650 sample. The size of the spherical nanoparticles is from 5 to 10 nm with the average size about 5 nm.

Examples 19-20. Comparative Examples. Procedures for the Preparation of Adducts of Silver (Ag) Nanoparticles (NPs) with CA-PyC Adducts, CA-PyC/Ag Adducts, with the Addition of a Reducing Agent Examples 19 and 20 are comparative examples: a reducing agent, such as glucose, was added to the reaction mixture.

Example 19: (COMPARISON). Mixture of HSAG-SP, Tollens' Reagent 350 UL and Glucose Tollens' reagent was prepared as follows: 1 mL of a 0.6 M $AgNO_3$ solution and 1 mL of a 2.8 M NaOH solution in distilled water ($dH_2O$) were mixed in a glass vial causing the formation of a brown precipitate, thus, $NH_4OH$ was added dropwise until a complete precipitate dissolution was achieved.

In a 15 mL falcon conical centrifuge tube, HSAG-SP (250 mg), glucose (10 mg) and $H_2O$ (5 mL) were sequentially added. The so obtained suspension was sonicated for 10 minutes using a 2 L ultrasound water bath. Afterwards, 350 μL of Tollens' reagent were added to the suspension. The mixture was then brought to volume (final volume: 7 mL) with distilled $H_2O$ and centrifuged (Refrigerated Centrifuge 3-16PK, Sigma Laborzentrifugen) at 4,000 rpm for 15 minutes (3×10 mL $H_2O$). The supernatant was removed and the black powder was dried. The formation of the silver mirror was observed on the walls of the glass test tube.

Example 20: (COMPARISON). Mixture of HSAG-SP, Tollens' Reagent 650 μL and Glucose Tollens' reagent was prepared as follows: 1 mL of a 0.6 M $AgNO_3$ solution and 1 mL of a 2.8 M NaOH solution in distilled water ($dH_2O$) were mixed in a glass vial causing the formation of a brown precipitate, thus, $NH_4OH$ was added dropwise until a complete precipitate dissolution was achieved.

In a 15 mL falcon conical centrifuge tube, HSAG-SP (250 mg), glucose (10 mg) and $H_2O$ (5 mL) were sequentially added. The so obtained suspension was sonicated for 10 minutes using a 2 L ultrasound water bath. Afterwards, 650 μL of Tollens' reagent were added to the suspension. The mixture was then brought to volume (final volume: 7 mL) with distilled $H_2O$ and centrifuged (Refrigerated Centrifuge 3-16PK, Sigma Laborzentrifugen) at 4,000 rpm for 15 minutes (3×10 mL $H_2O$). The supernatant was removed and the black powder was dried. The formation of the silver mirror was observed on the walls of the glass test tube.

The comparative examples 19-20 reveal that the addition of a reducing agent such as glucose leads to the formation of a silver mirror on the walls of the glass tube.

Such a mirror was not observed in Examples 7-18, which were performed without adding a reducing agent.

Examples 21-26. Comparative Examples. Pristine Carbon Allotropes (CA) and Tollens' Reagent Examples 21-26 are comparative examples. In the examples the formation of the adduct between CA-SP and Ag was attempted. The pristine carbon allotropes was used, hence not the adduct of the carbon allotrope with the pyrrole compound. A reducing agent was not added.

Example 21: Pristine CNT and Tollens' Reagent 350 μL

Pristine CNT was mixed with the Tollens' reagent following the procedure described in example 7, using pristine CNT instead of CNT-SP and 350 μL of Tollens' reagent. The formation of Ag nanoparticles was not observed.

Example 22: Pristine CNT and Tollens' Reagent 650 μL

Pristine CNT was mixed with the Tollens' reagent following the procedure described in example 7, using pristine CNT instead of CNT-SP and 650 μL of Tollens' reagent. The formation of Ag nanoparticles was not observed.

Example 23: Pristine HSAG and Tollens' Reagent 350 μL

Pristine HSAG was mixed with the Tollens' reagent following the procedure described in example 7, using pristine HSAG instead of CNT-SP and 350 μL of Tollens' reagent. The formation of Ag nanoparticles was not observed.

Example 24: Pristine HSAG and Tollens' Reagent 650 μL

Pristine HSAG was mixed with the Tollens' reagent following the procedure described in example 7, using pristine HSAG instead of CNT-SP and 650 μL of Tollens' reagent. The formation of Ag nanoparticles was not observed.

Example 25: Pristine CBN326 and Tollens' Reagent 350 μL

Pristine CBN326 was mixed with the Tollens' reagent following the procedure described in example 7, using pristine CBN326 instead of CNT-SP and 350 μL of Tollens' reagent. The formation of Ag nanoparticles was not observed.

Example 26: Pristine CBN326 and Tollens' Reagent 650 μL

Pristine CBN326 was mixed with the Tollens' reagent following the procedure described in example 7, using pristine CBN326 instead of CNT-SP and 650 μL of Tollens' reagent. The formation of Ag nanoparticles was not observed.

HRTEM Analysis

It was performed on samples from examples 22, 24 and 26. Micrographs are shown in FIG. 18.

FIG. 18—HRTEM micrographs for sample of example 22 (A), 24 (B) and 26 (C) (Comparison examples).

In FIG. 18A, CNT are clearly visible. Ag nanoparticles cannot be detected.

In FIG. 18B it is evident the highly disordered graphitic structure of HSAG-SP adducts. Ag nanoparticles cannot be detected.

Examples 27-32. Preparation of PBS Based Water CA-SP/Ag Suspensions

PBS is the Phosphate-Buffered Saline solution, which is the ideal biological environment per bacteria. In Examples 27-32, CA-SP/Ag adducts are added to PBS.

Example 27: PBS Based Water Suspensions of CNT-SP/Ag 350 Preparation

Water suspension of the product of example 7, is prepared as follow: $H_2O$ and PBS were added to an aliquot of the powder obtained in example 7: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Example 28: PBS Based Water Suspensions of CNT-SP/Ag 650 Preparation

Water suspension of the product of example 8, is prepared as follow: $H_2O$ and PBS were added to an aliquot of the powder obtained in example 8: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Example 29: PBS Based Water Suspensions of HSAG-SP/Ag 350 Preparation

Water suspension of the product of example 11, is prepared as follow: $H_2O$ and PBS were added to an aliquot of the powder obtained in example 11: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Example 30: PBS Based Water Suspensions of HSAG-SP/Ag 650 Preparation

Water suspension of the product of example 12, is prepared as follow: $H_2O$ and PBS were added to an aliquot of the powder obtained in example 12: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Example 31: PBS Based Water Suspensions of CBN326-SP/Ag 350 Preparation

Water suspension of the product of example 13, is prepared as follow: $H_2O$ and PBS were added to an aliquot of the powder obtained in example 13: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Example 32: PBS Based Water Suspensions of CBN326-SP/Ag 650 Preparation

Water suspension of the product of example 14, is prepared as follow: $H_2O$ and PBS were added to an aliquot of the powder obtained in example 14: suspensions at different concentrations have been obtained: 1 mg/mL, 0.5 mg/mL, 0.1 mg/mL, 0.05 mg/mL, 0.01 mg/mL, 0.005 mg/mL and 0.001 mg/mL. Each suspension was sonicated for 10 minutes using a 2 L ultrasonic bath (at 260 W) and subsequently the UV-Vis absorption was measured immediately after sonication.

Examples 33-41: Antimicrobial Activity Evaluation of CA-SP/Ag Suspensions

Example 33: Antimicrobial Activity Evaluation of CNT-SP/Ag 350 Suspension

Water suspension prepared as reported in example 27 was checked as antimicrobial agent by applying the method described above in the text (Biological assay, in the Method section).

Example 34: Antimicrobial Activity Evaluation of CNT-SP/Ag 650 Suspension

A water suspension of the product of example 28, was tested as reported in Example 33, using CNT-SP/Ag 650 instead of CNT-SP/Ag 350.

Example 35: Antimicrobial Activity Evaluation of CNT-SP Suspension

A water suspension of the product of Example 1 was tested as reported in Example 33, using CNT-SP instead of CNT-SP/Ag 350, maintaining the same concentration of SP.

Example 36: Antimicrobial Activity Evaluation of HSAG-SP/Ag 350 Suspension

A water suspension of the product of example 29 was tested as reported in Example 33, using HSAG-SP/Ag 350 instead of CNT-SP/Ag 350. In this test, the starting Ag concentration was equal to 600 μM, instead of 4 mM. 1:8 dilutions were then made. The following concentrations were obtained: 75 μM, 9.4 μM, 1.2 μM.

Example 37: Antimicrobial Activity Evaluation of HSAG-SP/Ag 650 Suspension

A water suspension of the product of example 30 was tested as reported in Example 33, using HSAG-SP/Ag 650 instead of CNT-SP/Ag 350. In this test, the starting Ag concentration was equal to 600 μM, instead of 4 mM. 1:8 dilutions were then made Example 38: Antimicrobial Activity Evaluation of HSAG-SP Suspension A water suspension of the product of Example 3 was tested as reported in Example 35, using HSAG-SP instead of HSAG-SP/Ag 350, maintaining the same concentration of SP.

Example 39: Antimicrobial Activity Evaluation of CBN326-SP/Ag 350 Suspension

A water suspension of the product of example 31, was tested as reported in Example 33, using CBN326-SP/Ag 350 instead of CNT-SP/Ag 350.

Example 40: Antimicrobial Activity Evaluation of CBN326-SP/Ag 650 Suspension

A water suspension of the product of example 32, was tested as reported in Example 33, using CBN326-SP/Ag 650 instead of CNT-SP/Ag 350.

Example 41: Antimicrobial Activity Evaluation of CBN326-SP Suspension

A water suspension of the product of Example 4 was tested as reported in Example 37, using CBN326-SP instead of CBN326-SP/Ag 350, maintaining the same concentration of SP.

The antimicrobial activity is expressed in terms of CFUs counts as a function of Sample Ag Molarity [μM]: the lower the CFU counts, the higher the antimicrobial effect of the product.

Antimicrobial Activity Evaluation for Samples Based on CNT-SP

In FIG. 19, there are culture plates at the end of the antimicrobial experiments. The plates refer to: 1: CNT-SP (Example 35), 2: CNT-SP/Ag350 (Example 33), 3: CNT-SP/Ag650 (Example 34). Each plate contains four sectors, each displaying CFU counts from diluted incubated suspensions. The sectors are as follows: A: incubated suspension from the rotatory mixer, without dilution, B: incubated suspension from the rotatory mixer with 1:10 dilution, C: incubated suspension from the rotatory mixer, with $1:10^2$ dilution, D: incubated suspension from the rotatory mixer, with $1:10^3$ dilution.

In FIG. 20, there is a graph showing the correlation between CFU counts and the Ag molar concentration of the suspensions, for suspensions based on CNT-SP/Ag350 and CNT-SP/Ag650. In the graph of FIG. 20, it is shown as well the curve referring to the CNT-SP sample, which does not contain Ag. However, a nominal Ag concentration was estimated on the basis of the following reasoning: (i) CNT-SP and CNT-SP/Ag350 are compared at the same SP content, (ii) the SP/Ag mass ratio in CNT-SP/Ag350 was used to estimate the nominal Ag content in CNT-SP. This way, an equivalent Ag Molarity was estimated.

Antimicrobial Activity Evaluation for Samples Based on HSAG-SP

In FIG. 21, there are culture plates at the end of the antimicrobial experiments. The plates refer to: 1: HSAG-SP (Example 38), 2: HSAG-SP/Ag350 (Example 36), 3: HSAG-SP/Ag650 (Example 37). Each plate contains four sectors, each displaying CFU counts from diluted incubated suspensions. The sectors are as follows: A: incubated suspension from the rotatory mixer, without dilution, B: incubated suspension from the rotatory mixer with 1:10 dilution, C: incubated suspension from the rotatory mixer, with $1:10^2$ dilution, D: incubated suspension from the rotatory mixer, with $1:10^3$ dilution.

In FIG. 22, there is a graph showing the correlation between CFU counts and the Ag molar concentration of the suspensions, for suspensions based on HSAG-SP/Ag350 and HSAG-SP/Ag650. In the graph of FIG. 22, it is shown as well the curve referring to the HSAG-SP sample, which does not contain Ag. However, a nominal Ag concentration was estimated on the basis of the following reasoning: (i) HSAG-SP and HSAG-SP/Ag350 are compared at the same SP content, (ii) the SP/Ag mass ratio in HSAG-SP/Ag350 was used to estimate the nominal Ag content in HSAG-SP. This way, an equivalent Ag Molarity was estimated.

Antimicrobial Activity Evaluation for Samples Based on CB-SP

In FIG. 23, there are culture plates at the end of the antimicrobial experiments. The plates refer to: 1: CB-SP (Example 41), 2: CB-SP/Ag350 (Example 39), 3: CB-SP/Ag650 (Example 40). Each plate contains four sectors, each displaying CFU counts from diluted incubated suspensions. The sectors are as follows: A: incubated suspension from the rotatory mixer, without dilution, B: incubated suspension from the rotatory mixer with 1:10 dilution, C: incubated suspension from the rotatory mixer, with $1:10^2$ dilution, D: incubated suspension from the rotatory mixer, with $1:10^3$ dilution.

In FIG. 24, there is a graph showing the correlation between CFU counts and the Ag molar concentration of the suspensions, for suspensions based on CB-SP/Ag350 and CB-SP/Ag650. In the graph of FIG. 24, it is shown as well the curve referring to the CB-SP sample, which does not contain Ag. However, a nominal Ag concentration was estimated on the basis of the following reasoning: (i) CB-SP and CB-SP/Ag350 are compared at the same SP content, (ii) the SP/Ag mass ratio in CB-SP/Ag350 was used to estimate the nominal Ag content in CB-SP. This way, an equivalent Ag Molarity was estimated.

The results obtained with the Examples 33-41 demonstrate the remarkable antibacterial activity of the adducts of CA-SP with $Ag^0$, dramatically larger than the activity of the CA-SP adducts.

In FIG. 25, the correlation between the CFU counts and the Ag molar concentration of the suspensions is shown for suspensions based on HSAG-SP/Ag350, CNT-SP/Ag350, CB-SP/Ag350.

In FIG. 26, the correlation between the CFU counts and the Ag molar concentration of the suspensions is shown for suspensions based on HSAG-SP/Ag350, CNT-SP/Ag350, CB-SP/Ag350.

The comparisons shown in FIG. 25 and in FIG. 26 reveal that the Ag based adducts have remarkably higher antimicrobial activity when HSAG and CNT are the $sp^2$ carbon allotropes.

HSAG based adducts reveal higher antimicrobial activity with respect to the CNT based adducts in the “350” series, whereas the HSAG and CNT based adducts have similar activities in the “650” series.

Minimal Bactericidal Concentration

The Minimal Bactericidal Concentration (MBC), which is usually indicated as the concentration of antibacterial agent necessary to kill at least 99.9% of bacterial cells, was evaluated, on the basis of the results of Examples 33-41. Values of MBC in Table 3 are expressed as Ag molarity and as adduct concentration.

TABLE 3

MBC values for CA-SP, CA-SP/Ag 350 and CA-SP/Ag 650 adducts.

| Carbon allotrope/ Adduct | Ag molarity [μM] | Adduct concentration [μg/mL] |
|---|---|---|
| HSAG-SP | / | / |
| HSAG-SP/Ag 350 | 37 | 88 |
| HSAG-SP/Ag 650 | 56 | 95 |
| CB-SP | / | / |
| CB-SP/Ag 350 | 1237 | 817 |
| CB-SP/Ag 650 | 1930 | 779 |
| CNT-SP | / | / |
| CNT-SP/Ag 350 | 294 | 185 |
| CNT-SP/Ag 650 | 50 | 31 |

It was not possible to estimate the MBC for the adducts HSAG-SP, CNT-SP, CB-SP, that means for the adducts without $Ag^0$.

From the data in Table 3, it is apparent that samples of the ‘350’ series are more effective than samples of the ‘650’ series, for HSAG-SP and CB-SP. This result indicates that the best antibacterial effect can be obtained by using a lower Ag amount, thus avoiding top waste reagents.

The invention claimed is:

1. An adduct of a metal selected from the group consisting of: copper, silver, gold, or mixture thereof; with an adduct of:

a $sp^2$ carbon allotrope and/or its derivative selected from the group consisting of:

carbon black, fullerene, Buchminstefullerenes, carbon nanohorns, single-walled carbon nanotubes, multi-walled carbon nanotubes, carbon nanobuds, graphene, bilayer graphene, few-layer graphene, graphenylene, ciclocarbons, and graphites with a number of stacked graphene layers from 2 to 10000, and/or its derivative containing functional groups selected from the group consisting of:

functional groups containing oxygen, hydroxyls, or epoxies;

functional groups containing carbonyls, aldehydes, ketones, or carboxylic acids;

functional groups containing nitrogen atoms, amines, amides, nitriles, diazonium salts, or imines;

functional groups containing sulfur atoms, sulfides, disulfides, sulfinates, sulfoxides, mercaptans, sulfones, sulfinic, sulfoxylic, or sulfonic groups;

with a compound of formula (I)

(I)

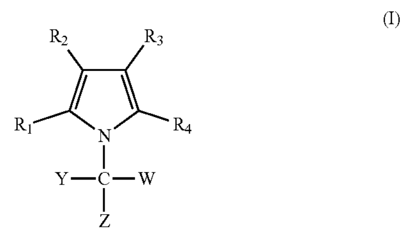

wherein $R_1$, $R_2$, $R_3$, $R_4$ are independently selected from the group consisting of: hydrogen, alkyl $C_1$-$C_3$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkynyl-aryl $C_2$-$C_6$ linear or branched, and heteroaryl, and Y, Z, and W are independently selected from the group consisting of hydrogen, alkyl $C_1$-$C_6$, and alkenyl or alkynyl $C_2$-$C_6$ linear or branched, or selected from the group consisting of:

(A)

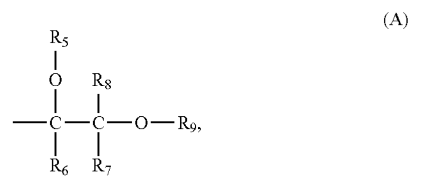

(B)

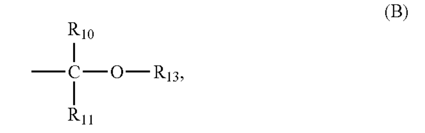

(C)

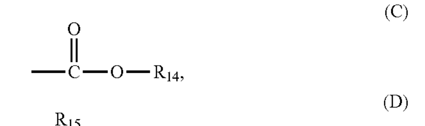

(D)

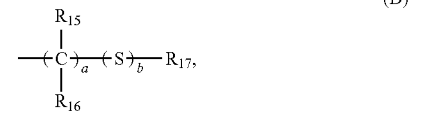

(E)

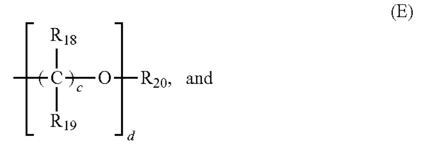

and

-continued (F)

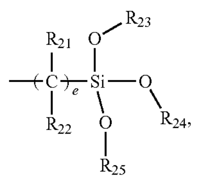

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, are independently selected from the group consisting of hydrogen, alkyl $C_1$-$C_6$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkenyl-aryl $C_2$-$C_6$ linear or branched, heteroaryl, and carboxyl, and wherein b is an integer from 1 to 4 and a, c, d and e are, independently, integers from 1 to 12.

2. The adduct according to claim 1, wherein the metal is silver.

3. The adduct according to claim 1, wherein the $R_1$, $R_2$, $R_3$, and $R_4$ are independently selected from the group consisting of: H, $CH_3$, $CH_2CH_3$, $CH_2CH_2CH_3$, and phenyl.

4. A process for the preparation of an adduct according to claim 1, comprising the steps of:

i. providing a solution and/or suspension of a compound of formula (I) in a protic or aprotic polar solvent;

ii. providing a mixture of the carbon allotrope in a protic or aprotic polar solvent used for the preparation of the solution and/or suspension referred to in step i.;

iii. mixing said solution and/or suspension (i) and said mixture (ii);

iv. stirring;

v. if necessary, removing said solvent from the obtained mixture;

vi. providing energy;

vii. if necessary, dispersing the obtained mixture in the protic or aprotic polar solvent;

viii. adding a salt of a transition metal soluble in the selected protic or aprotic polar solvent;

ix. stirring;

x. if necessary, removing said solvent from the obtained mixture.

5. The process according to claim 4, further comprising:

xi. if necessary, dispersing the mixture obtained after step vi in the protic or aprotic polar solvent;

xii. adding a reducing agent;

xiii. stirring;

xiv. removing said solvent from the obtained mixture.

6. The process according to claim 5, wherein the reducing agent is selected from the group consisting of: alcohols, aldehydes, and carboxylic acids.

7. The process according to claim 5, wherein the reducing agent is present in an equimolar amount with respect to the salt of the transition metal.

8. An adduct of a metal selected from the group consisting of: copper, silver, gold, or mixture thereof; with an adduct of:

a $sp^2$ carbon allotrope and/or its derivative, wherein the derivative of said carbon allotrope is graphite oxide, and compound of formula (I)

(I)

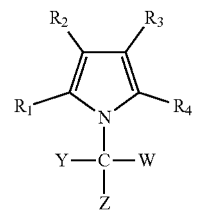

wherein $R_1$, $R_2$, $R_3$, $R_4$ are independently selected from the group consisting of: hydrogen, alkyl $C_1$-$C_3$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkynyl-aryl $C_2$-$C_6$ linear or branched, and heteroaryl, and Y, Z, and W are independently selected from the group consisting of hydrogen, alkyl $C_1$-$C_6$, and alkenyl or alkynyl $C_2$-$C_6$ linear or branched, or selected from the group consisting of:

(A)

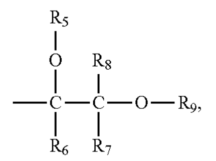

(B)

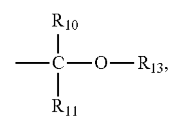

(C)

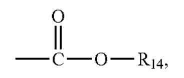

(D)

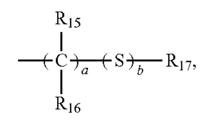

(E)

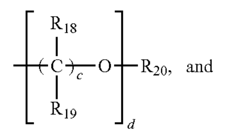

(F)

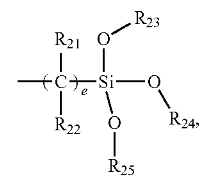

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, are independently selected from the group consisting of hydrogen, alkyl $C_1$-$C_6$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkenyl-aryl $C_2$-$C_6$ linear or branched, heteroaryl, and carboxyl, and wherein b is an integer from 1 to 4 and a, c, d and e are, independently, integers from 1 to 12.

9. The adduct according to claim 8, wherein the metal is silver.

10. The adduct according to claim 8, wherein the $R_1$, $R_2$, $R_3$, and $R_4$ are independently selected from the group consisting of: H, $CH_3$, $CH_2CH_3$, $CH_2CH_2CH_3$, and phenyl.

11. A process for the preparation of an adduct according to claim 8, comprising the steps of:
i. providing a solution and/or suspension of a compound of formula (I) in a protic or aprotic polar solvent;
ii. providing a mixture of the carbon allotrope in a protic or aprotic polar solvent used for the preparation of the solution and/or suspension referred to in step i.;
iii. mixing said solution and/or suspension (i) and said mixture (ii);
iv. stirring;
v. if necessary, removing said solvent from the obtained mixture;
vi. providing energy;
vii. if necessary, dispersing the obtained mixture in the protic or aprotic polar solvent;
viii. adding a salt of a transition metal soluble in the selected protic or aprotic polar solvent;
ix. stirring;
x. if necessary, removing said solvent from the obtained mixture.

12. The process according to claim 11, further comprising:
xi. if necessary, dispersing the mixture obtained after step vi in the protic or aprotic polar solvent;
xii. adding a reducing agent;
xiii. stirring;
xiv. removing said solvent from the obtained mixture.

13. The process according to claim 12, wherein the reducing agent is selected from the group consisting of: alcohols, aldehydes, and carboxylic acids.

14. The process according to claim 12, wherein the reducing agent is present in an equimolar amount with respect to the salt of the transition metal.

15. An adduct of a metal selected from the group consisting of: copper, silver, gold, or mixture thereof; with an adduct of:
a $sp^2$ carbon allotrope and/or its derivative, wherein the derivative of said carbon allotrope is graphene oxide, and compound of formula (I)

(I)

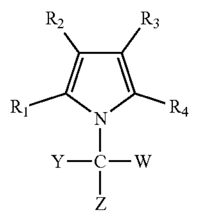

wherein $R_1$, $R_2$, $R_3$, $R_4$ are independently selected from the group consisting of: hydrogen, alkyl $C_1$-$C_3$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkynyl-aryl $C_2$-$C_6$ linear or branched, and heteroaryl,
and
Y, Z, and W are independently selected from the group consisting of hydrogen, alkyl $C_1$-$C_6$, and alkenyl or alkynyl $C_2$-$C_6$ linear or branched, or selected from the group consisting of:

(A)

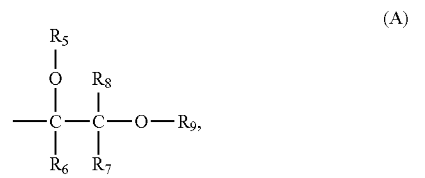

(B)

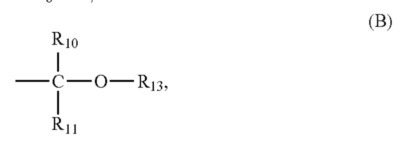

(C)

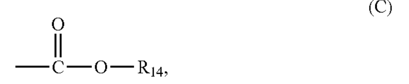

(D)

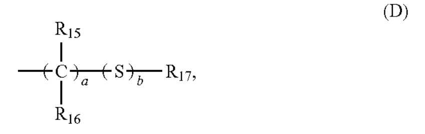

(E)

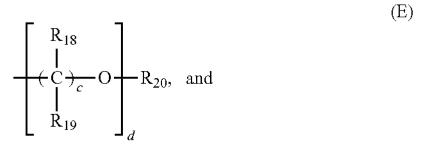

and (F)

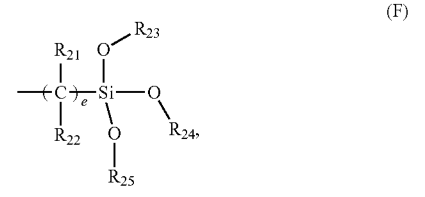

wherein $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, are independently selected from the group consisting of hydrogen, alkyl $C_1$-$C_6$, alkenyl or alkynyl $C_2$-$C_6$ linear or branched, aryl, alkyl-aryl $C_1$-$C_6$ linear or branched, alkenyl-aryl $C_2$-$C_6$ linear or branched, alkenyl-aryl $C_2$-$C_6$ linear or branched, heteroaryl, and carboxyl, and
wherein b is an integer from 1 to 4 and a, c, d and e are, independently, integers from 1 to 12.

16. The adduct according to claim 15, wherein the metal is silver.

17. The adduct according to claim 15, wherein the $R_1$, $R_2$, $R_3$, and $R_4$ are independently selected from the group consisting of: H, $CH_3$, $CH_2CH_3$, $CH_2CH_2CH_3$, and phenyl.

18. A process for the preparation of an adduct according to claim 8, comprising the steps of:
i. providing a solution and/or suspension of a compound of formula (I) in a protic or aprotic polar solvent;
ii. providing a mixture of the carbon allotrope in a protic or aprotic polar solvent used for the preparation of the solution and/or suspension referred to in step i.;
iii. mixing said solution and/or suspension (i) and said mixture (ii);
iv. stirring;
v. if necessary, removing said solvent from the obtained mixture;
vi. providing energy;
vii. if necessary, dispersing the obtained mixture in the protic or aprotic polar solvent;

viii. adding a salt of a transition metal soluble in the selected protic or aprotic polar solvent;

ix. stirring;

x. if necessary, removing said solvent from the obtained mixture.

* * * * *